(12) United States Patent
Baram et al.

(10) Patent No.: US 11,937,975 B2
(45) Date of Patent: Mar. 26, 2024

(54) MULTI-FREQUENCY MAPPING CATHETER AND METHOD OF MAPPING

(71) Applicant: Biosense Webster (Israel) Ltd., Yokneam (IL)

(72) Inventors: Alon Baram, Yokneam Ilit (IL); Zvi Menachem Friedman, Petach Tiqua (IL); Meir Bar-Tal, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 153 days.

(21) Appl. No.: 17/025,622

(22) Filed: Sep. 18, 2020

(65) Prior Publication Data

US 2021/0093292 A1 Apr. 1, 2021

Related U.S. Application Data

(60) Provisional application No. 62/908,204, filed on Sep. 30, 2019.

(51) Int. Cl.
*A61B 8/12* (2006.01)
*A61B 8/00* (2006.01)
*A61B 8/08* (2006.01)

(52) U.S. Cl.
CPC .............. *A61B 8/12* (2013.01); *A61B 8/0883* (2013.01); *A61B 8/4494* (2013.01); *A61B 8/461* (2013.01)

(58) Field of Classification Search
CPC ....... A61B 8/12; A61B 8/0883; A61B 8/4494; A61B 8/461; A61B 8/4477; A61B 8/445;
(Continued)

(56) References Cited

U.S. PATENT DOCUMENTS 4,841,977 A 6/1989 Griffith et al.
6,004,269 A 12/1999 Crowley et al.
(Continued)

FOREIGN PATENT DOCUMENTS

WO 92/16140 A1 10/1992
WO WO-1992016140 A1 * 10/1992 ........... A61B 18/245
WO WO-2012053514 A1 * 4/2012 ............... A61B 8/06

OTHER PUBLICATIONS

Calkins, H., et al.: "2017 HRS/EHRA/ECAS/APHRS/SOLAECE expert consensus statement on catheter and surgical ablation of atrial fibrillation," Europace 20(1), e1-e160 (2018).
(Continued)

*Primary Examiner* — Sean D Mattson
*Assistant Examiner* — Michael Yiming Fang
(74) *Attorney, Agent, or Firm* — Volpe Koenig P.C.

(57) ABSTRACT

The present disclosure provides systems, apparatuses and methods that include a catheter configured to be inserted into an intra-body cavity of a patient. An ultrasonic transducer array including a plurality of multi-frequency ultrasonic transducers may be arranged on the catheter. Each of the plurality of multi-frequency ultrasonic transducers may be configured to transmit a wide beam ultrasonic signal and a narrow beam ultrasound signal, and may further be configured to receive a wide beam echo signal and narrow beam echo signal. A processor may be configured to detect free space of the intra-body cavity by processing the wide beam echo signals and the narrow beam echo signals.

20 Claims, 30 Drawing Sheets

(58) Field of Classification Search
CPC .............. A61B 18/12; A61B 8/4483; A61B 2018/00267; A61B 2018/00351; A61B 8/4281; A61B 8/44; A61B 8/4427; A61B 8/4444; A61B 8/4405; A61B 5/0816; A61B 5/0022; A61B 5/0205; A61B 5/024; A61B 5/113; A61B 5/28; A61B 5/6823; A61B 5/6824; A61B 5/6831; A61B 5/7405; G01S 15/8977; G01S 7/52085; G01S 15/8952; G01S 15/8915

See application file for complete search history.

(56) References Cited

U.S. PATENT DOCUMENTS

| | | | |
|---|---|---|---|
| 6,592,520 | B1 | 7/2003 | Peszynski et al. |
| 9,576,107 | B2 | 2/2017 | Safran et al. |
| 2003/0028107 | A1 | 2/2003 | Miller et al. |
| 2009/0209857 | A1* | 8/2009 | Secretain .............. A61B 8/0833 600/437 |
| 2010/0167251 | A1 | 7/2010 | Boutchko et al. |
| 2010/0249590 | A1* | 9/2010 | Kanayama .......... G01S 15/8963 600/442 |
| 2011/0237951 | A1* | 9/2011 | Bandy ................. G10K 11/346 367/137 |
| 2012/0027278 | A1 | 2/2012 | Chaney et al. |
| 2014/0088429 | A1* | 3/2014 | Lomes ................... A61B 8/145 600/443 |
| 2016/0324502 | A1* | 11/2016 | Lu ............................ A61B 8/12 |
| 2016/0338724 | A1* | 11/2016 | Sinelnikov ............. A61B 8/445 |
| 2019/0053783 | A1* | 2/2019 | Stigall .................... A61N 7/022 |
| 2019/0133557 | A1* | 5/2019 | Liu ....................... G01S 7/52074 |
| 2019/0209089 | A1 | 7/2019 | Baram et al. |
| 2019/0282200 | A1* | 9/2019 | Choi ................... G01S 15/8925 |
| 2020/0179062 | A1* | 6/2020 | Hunter ................. A61B 8/0841 |
| 2020/0268343 | A1* | 8/2020 | Zhou ...................... A61B 8/469 |
| 2020/0273169 | A1* | 8/2020 | Mauldin ................ G06T 7/0012 |
| 2020/0315584 | A1* | 10/2020 | Wissel ..................... A61B 8/08 |

OTHER PUBLICATIONS

Ye et al., "Shape-Based Ct Lung Nodule Segmentation Using Five-Dimensional Mean Shift Clustering and Mem with Shape Information", IEEE (2009).

Kliger, C., Cruz-Gonzalez, I., Ruiz, C.E.: "The present and future of intracardiac echocardiography for guiding structural heart disease interventions", Revista Española de Cardiologia (English Edition) 65(09), 791-794 (2012).

Knackstedt, C., Schauerte, P., Kirchhof, P.: "Electro-anatomic mapping systems in arrhythmias", EP Europace 10 (suppl-3), iii28-iii34 (2008).

Liao, H., Tang, Y., Funka-Lea, G., Luo, J., Zhou, S.K.: "More knowledge is better: cross-modality volume completion and 3D+2D segmentation for intracardiac echocardiography contouring", In: Frangi, A.F., Schnabel, J.A., Davatzikos, C., Alberola-López, C., Fichtinger, G. (eds.) MICCAI 2018. LNCS, vol. 11071, pp. 535-543. Springer, Cham (2018).

Nazarian, S., et al.: "Direct visualization of coronary sinus ostium and branches with a flexible steerable fiberoptic infrared endoscope", Heart Rhythm 2(8), 844-848 (2005).

Pellman, J., Sheikh, F.: "Atrial fibrillation: mechanisms, therapeutics, and future directions", Compr. Physiol. 5(2), 649-665 (2015).

Baram et al., "A Sparsely Distributed Intra-cardial Ultrasonic Array for Real-Time Endocardial Mapping." ECCV 2012, p. 272-280 (2019).

Extended European Search Report dated Dec. 17, 2020 for European Patent Application No. 20199023.1.

* cited by examiner

Equation 9: $$W_{i,j} = s_{i,\phi} \cap s_{j,\phi}$$

FIG. 19A

Equation 10: $$y_0 = \pm \frac{b}{a}\sqrt{a^2 - x_0^2}$$

$$\frac{\left(\left(\frac{1}{2}(-p_{1x} - p_{2x}) + x_0\right)\sin(\angle(p_1 - p_2)) - \left(\frac{1}{2}(-p_{1y} - p_{2y}) + y_0\right)\cos(\angle(p_1 - p_2))\right)^2}{a_\theta^2 + \frac{1}{4}\left(-|p_{2x} - p_{1x}|^2 - |p_{2y} - p_{1y}|^2\right)}$$

$$+ \frac{\left(\left(\frac{1}{2}(-p_{1x} - p_{2x}) + x_0\right)\cos(\angle(p_1 - p_2)) + \left(\frac{1}{2}(-p_{1y} - p_{2y}) + y_0\right)\sin(\angle(p_1 - p_2))\right)^2}{a_\theta^2} = 1$$

FIG. 19B

Equation 11:

$$\mp a_\theta b \sqrt{a^2 - x_0^2 - a_\theta^2 + a_\theta^2 \cos(\theta)(\sin(\theta)(u - x_0) + \cos(\theta)(y_0 - v))} +$$

$$a_\theta^2 \sin(\theta)(\sin(\theta)(u - x_0) + \cos(\theta)(y_0 - v)) + a_\theta^2 x_0 - b_\theta^2 \cos(\theta)(\cos(\theta)(x_0 - u) + \sin(\theta)(y_0 - v)) - v = 0$$

$$\frac{1}{4}\left(-|p_{2x} - p_{1x}|^2 - |p_{2y} - p_{1y}|^2\right) + a_\theta^2 = b_\theta^2 \quad (4)$$

FIG. 19C

Equation 12: $$S(s, re, sc, t) = \frac{\phi(s, re, sc, t - t_d) Dir(\Theta_{s, sc}, k a) Dir(\Theta_{sc, re}, ka)}{16\pi^2 \|x_s - x_{sc}\| \|x_{sc} - x_{re}\|}$$

FIG. 19D

Equation 13: $$\psi(s, re, t) = \sum_{sc} P_1(x_{sc}) S(s, sc, re, t)$$

FIG. 19E

Equation 14: $$DAS(\vec{x}) = \sum_{s, re, t \mid t_d = t, sc \in \vec{x}} \psi(s, re, t)$$

FIG. 19F

Equation 15: $$T = \frac{1}{c}\left(\|x_s - \vec{x}\| + \|\vec{x} - x_{re}\|\right)$$

FIG. 19G

Equation 16:
$$\mathcal{E}(S) \leq \frac{P_0 Dir(\Theta_{s,sc,ka}) Dir(\Theta_{sc,re,ka})}{16\pi^2 \|x_s - x_{sc}\| \|x_{sc} - x_{re}\|} = \mathcal{E}^*(S)$$

FIG. 19H

Equation 17:
$$P_1(x_{sc}) S(s, sc, re, t = t_d) \leq P_1(x_{sc}) \mathcal{E}^*(S) \leq$$
$$\tilde{S} = \sum_{sc' \in E(s,sc,re))} P_1(x_{sc'}) \mathcal{E}(S(s, sc', re)) = \mathcal{E}(\psi(s, re, t = t_d))$$

FIG. 19I

Equation 18:
$$P_1(x_{sc}) \leq \min_{s,re \in \Omega} \frac{\tilde{S}(s, re, sc)}{\mathcal{E}^*(S)}$$

FIG. 19J

Equation 19:
$$\rho(\vec{X}) = \min_{s,re | \vec{X} \in E(s,re,sc); s,re \in \Omega} \frac{\mathcal{E}(\psi(s, re, t = t_d))}{\mathcal{E}^*(S)}$$

FIG. 19K

MULTI-FREQUENCY MAPPING CATHETER AND METHOD OF MAPPING

INCORPORATION BY REFERENCE

This application claims the benefit of U.S. Provisional Application No. 62/908,204, filed on Sep. 30, 2019, which is incorporated by reference as if fully set forth.

FIELD OF INVENTION

The present application provides systems, apparatuses, and methods for mapping inter-body cavities.

BACKGROUND

Medical conditions such as cardiac arrhythmia (e.g., atrial fibrillation (AF)) are often treated via intra-body procedures. For example, electrical pulmonary vein isolation (PVI) from the left atrial (LA) body is performed using ablation for treating AF. PVI, and many other minimally invasive catheterizations, require real-time visualization and tracking of an intra-body surface.

Visualization and tracking of intra-body surfaces can be performed by mapping propagation of activation waves, Fluoroscopies, computerized tomography (CT) and magnetic resonance imaging (MRI), as well as other techniques which may require a high amount of time or resources to provide the visualization and tracking.

SUMMARY

The present disclosure provides systems, apparatuses and methods that include a catheter configured to be inserted into an intra-body cavity of a patient. An ultrasonic transducer array including a plurality of multi-frequency ultrasonic transducers may be arranged on the catheter. Each of the plurality of multi-frequency ultrasonic transducers may be configured to transmit a wide beam ultrasonic signal and a narrow beam ultrasound signal, and each of the plurality of multi-frequency ultrasonic transducers may be further configured to receive a wide beam echo signal and narrow beam echo signal in response to the wide beam ultrasonic signal and a narrow beam ultrasound signal, respectively.

In one aspect, a processor is configured to identify free space in the intra-body cavity by processing the wide beam echo signals and the narrow beam echo signals.

BRIEF DESCRIPTION OF THE DRAWINGS

A more detailed understanding can be had from the following description, given by way of example in conjunction with the accompanying drawings wherein:

FIGS. 19A through 19K illustrate equations 9 through 19 for clarity, respectively.

DETAILED DESCRIPTION

Figure 1:
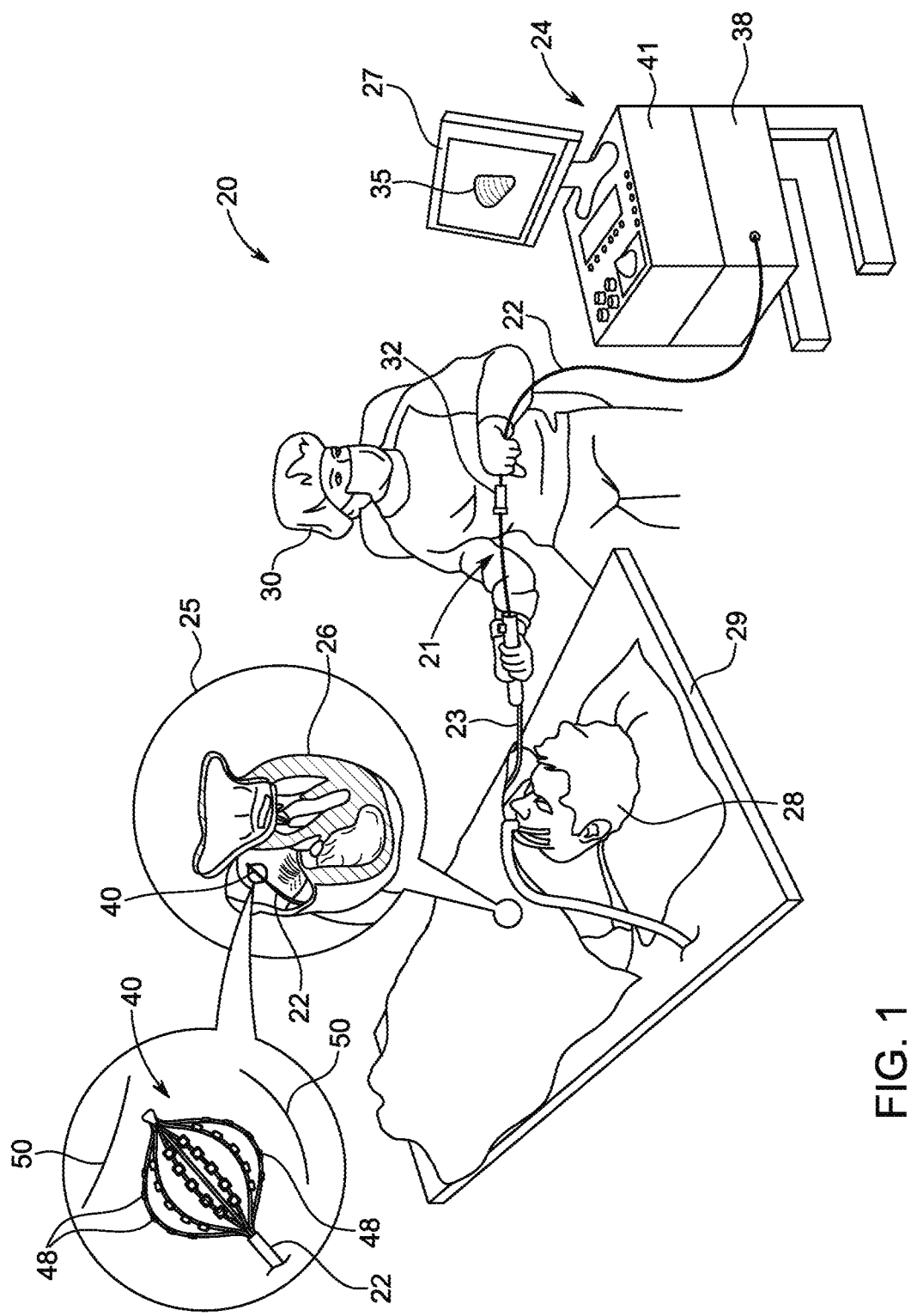
FIG. 1 is an example diagram of a catheter-based cardiac mapping system.

As disclosed herein, the systems, apparatuses and methods provide instant localization of a large quantity (e.g., thousands) of points on a surface, such as an endocardial surface. The disclosed subject matter provides images and reconstruction that are comparable to the details provided by an MRI.

According to embodiments of the disclosed subject matter, systems and methods that produce a spatial map of an intra-body cavity, such as a cardiac chamber, with enhanced contrast, while employing fast acquisition and reconstruction schemes, are provided.

An array of ultrasound transducers (e.g., 64 transducers) is provided which are configured to transmit both wide and narrow beams and receive corresponding scattered wide and narrow beams. The wide beams are used to map wide portions of intra-body chambers such as the surface of a cardiac chamber. The narrow beams are used to map narrow portions of intra-body chambers such as the veins that lead to and from a cardiac chamber.

As used herein, the term "wide" as used with respect to the term wide beam or wide beam ultrasonic signal may have a frequency in the range of 1 MHz to 3 MHz. In one embodiment, the term wide beam refers to a signal having a frequency within +1-50% of 1.4 MHz. As used herein, the term "narrow" as used with respect to the term narrow beam or narrow beam ultrasonic signal may have a frequency in the range of 5 MHz to 9 MHz, or 12 MHz to 16 MHz. In one embodiment, the term narrow beam refers to a signal having a frequency within +1-50% of 7.4 MHz.

A wide beam or a wide beam ultrasonic signal may include a beam width in the range of 100 degrees to 150 degrees. In one aspect, the wide beam has a width of at least 40 degrees or greater. A narrow beam or a narrow beam ultrasonic signal may include a beam width in the range of 4 degrees to 12 degrees. One of ordinary skill in the art would understand that depending on the specific medium in which the beams are being transmitted or the geometry which is being mapped, the exact values for wide and narrow beams may vary.

Although a 64-element transducer array is described herein, one of ordinary skill in the art would understand that number of transducers can vary and can include less than 64 transducers or more than 64 transducers.

The embodiments disclosed herein include an ultrasonic mapping system along with an algorithm that accurately maps an entire endocardial chamber surface at a single glance (e.g., a single heart beat). Such mapping, along with simultaneous mapping of electrical activity at all points on the chamber's surface results in a significant reduction of the overall procedural time in all scenarios, including complex arrhythmias. The disclosed subject matter provides the ability to reconstruct anatomy within a few scans due to scanning the entire space volume with beams of different patterns, and composing this information quickly to find a chamber's boundary.

Arrays of multi-frequency ultrasonic transducers mounted on geometrically shaped catheters (e.g., basket shaped spherical catheter) are disclosed. The arrays allow geometrical mapping of an entire endocardial surface, including the ostia of pulmonary veins, as well as other veins and small components associated with endocardial surfaces. The endocardial surface may be mapped using a non-linear ellipsoidal extended Radon back-projection, as further disclosed herein.

In some embodiments, an ultrasonic spatial mapping basket catheter is provided. The ultrasound basket catheter may be capable of acquiring data to map an entire surface of a cardiac chamber from a single position in the cardiac chamber, e.g., without having to be rotated or moved across the chamber in the process. An improved reconstruction method is also provided, to be used with the ultrasound basket catheter, which enables reconstructing and presenting a spatial map that visualizes the enhanced contrast within a chamber, including major myocardium surfaces as well as narrower surfaces such as veins (e.g., pulmonary veins).

In some embodiments, the ultrasound basket catheter may be fitted with multiple multi-frequency ultrasonic transducers coupled to splines that form the basket shape. The transducers are distributed sparsely over the splines, and operate in Amplitude mode (A-mode) in order to generate and acquire echo signals. These echo signals are subsequently processed by a processor and used to prepare a mapping of the heart. In one aspect, the processor uses a free space method. In another embodiment, the processor uses an ellipsoidal back-projection method to rapidly produce spatial maps. Generally, the ellipsoidal back-projection method essentially is the same as synthetic aperture beam forming, which is the same as delay and sum beam forming. This type of projection operates on the following principles. If a point in space is examined using an array, it is possible to transmit from all of the transducers of the array with time delays such that all the waves will hit this point at the same time. This concept involves transmitting focus to a point. The same concept can be used for receiving beams or echoes. Instead of transmitting and receiving beams physically, these events can be done via software because acoustic waves are linear in nature. Accordingly, transmitting from a first transducer and receiving the echo or response signal at all of the other transducers of the array, and then doing the same for the second transducer, the third transducer, and so on. Data is collected from all of the transducers. When focusing to a point, a shift in time is carried out such that all the signals hit a point simultaneously or at the same time. The reflectivity value of this point is the summation of those time shifted signals at the appropriate time value. This concept is incorporated into the bounding reflection value (BRV), which is described in more detail herein.

In one aspect, the free space mapping method disclosed herein is a variation or modification of an ellipsoidal back-projection method. The method of ellipsoidal back-projection uses synthetic apertures to align beams in time in order to focus the beams using a computation to find reflectivity of a small region in space. The disclosed subject matter finds an upper bound of reflectivity, which provides for a more robust imagining technique.

Wide beam echo signals are used to map major myocardium surfaces and narrow beam signals are used to map narrow surfaces such as veins. The term multi-frequency transducer is used herein to refer to a transducer configured to emit more than one frequency. In one embodiment, the multi-frequency transducers are dual frequency transducers, i.e. two or double frequency transducers. In other embodiments, the multi-frequency transducers emit more than two frequencies.

The ellipsoidal back-projection method, as disclosed, assumes to have a finite number of transmitting/receiving ultrasound transducers where each transducer transmits an echo signal one at a time while all transducers receive scattered echo signals. In one aspect, these signals are transmitted in a few microseconds. Acquisition time is dictated by how large of area is being imaged. In one embodiment, a parameter set period is around 70 microseconds for a range of about 4 cm per transmit receive event. The location of scatters in the volume and the reflected amplitudes from the scatters are calculated based on ellipsoidal calculations.

The accuracy of a spatial map of a cardiac chamber benefits from faster acquisition and reconstruction times. In an embodiment, the disclosed method shortens calculation times by producing a synthetic spatial map, which is based on analyzing single dimensional A-mode signals, rather than attempting to perform an unnecessary and computationally-demanding full image reconstruction. The disclosed systems and methods, which combine (i) a basket ultrasound array that instantaneously acquires multiple ultrasound measurements and (ii) an improved reconstruction scheme including wide and narrow beam signals, may be advantageous to the physician, who may receive more accurate spatial and functional maps of an intra-body cavity, such as a cardiac chamber. Hence, the disclosed system and method may enable the physician to perform efficient invasive diagnostics and possibly subsequent treatment sessions.

FIG. 1 is an illustration of a catheter-based cardiac mapping system 20 comprising an ultrasound basket catheter 40, in accordance with one embodiment. It will be understood that although a basket shape is disclosed throughout, any shape catheter comprising multiple transducers may be used to implement the embodiments disclosed herein. The system 20 comprises a catheter 21, having a shaft 22 that may be navigated by a physician 30 into a heart 26 of a patient 28 lying on a table 29. As shown in FIG. 1, the physician 30 may insert the shaft 22 through a sheath 23, while manipulating the distal end of the shaft 22 using a manipulator 32 near the proximal end of the catheter and/or deflection from the sheath 23. As shown in an inset 25, the basket catheter 40 may be fitted at the distal end of the shaft 22. The basket catheter 40 may be inserted through the sheath 23 in a collapsed state and may be then expanded within the heart 26.

In an embodiment, the basket catheter 40 may be configured to perform spatial mapping of a cardiac chamber of the heart 26 by transmitting wide and narrow echo signals and receiving wide and narrow echo signals that were reflected from cardiac chamber surfaces 50. An inset 45 shows the basket catheter 40 in an enlarged view, inside a cardiac chamber of the heart 26. As shown, the basket catheter 40 may include an array of ultrasound transducers 48 coupled onto splines that form the basket shape.

The proximal end of the catheter 21 may be connected to a console 24. The console 24 may include a processor 41, such as a general-purpose computer, with suitable front end and interface circuits 38 for transmitting and receiving signals to and from the catheter 21, as well as for controlling the other components of the system 20. In some embodiments, the processor 41 may be further configured to receive multi-frequency (e.g., wide and narrow) echo signals and to calculate a map of a surface of a cardiac chamber from the echo signals. In one aspect, the processor 41 is configured to identify a first area of the intra-body cavity by processing the wide beam echo signals, and identify a second area of the intra-body cavity by processing the narrow beam echo signals. In other words, the wide beam echo signals are configured to specifically map certain portions of the cavity and the narrow beam echo signals are configured to specifically map other portions of the cavity. When used in combination, both sets of echo signals provide a complete mapping of the cavity.

In an embodiment, the surface of the surrounding anatomy may be presented to the physician 30 on a display 27, e.g., in a graphical form of a mesh diagram 35.

As noted above, the processor 41 may include a general-purpose computer, which may be programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. The example configuration shown in FIG. 1 is chosen for the sake of conceptual clarity. The disclosed subject matter herein can be used in a variety of applications, not just limited to mapping a patient's heart and not just limited to mapping anatomical objects. The disclosed techniques may similarly be applied using other system components and settings. Additionally, the system 20 may include additional components, such as ones for electrophysiological mapping and/or ablation. Although the pictured embodiment relates specifically to the use of an ultrasound basket catheter for cardiac mapping, the elements of the system 20 and the methods described herein may alternatively be applied in ultrasound mapping using catheters having other multi-arm geometries.

Figure 2:
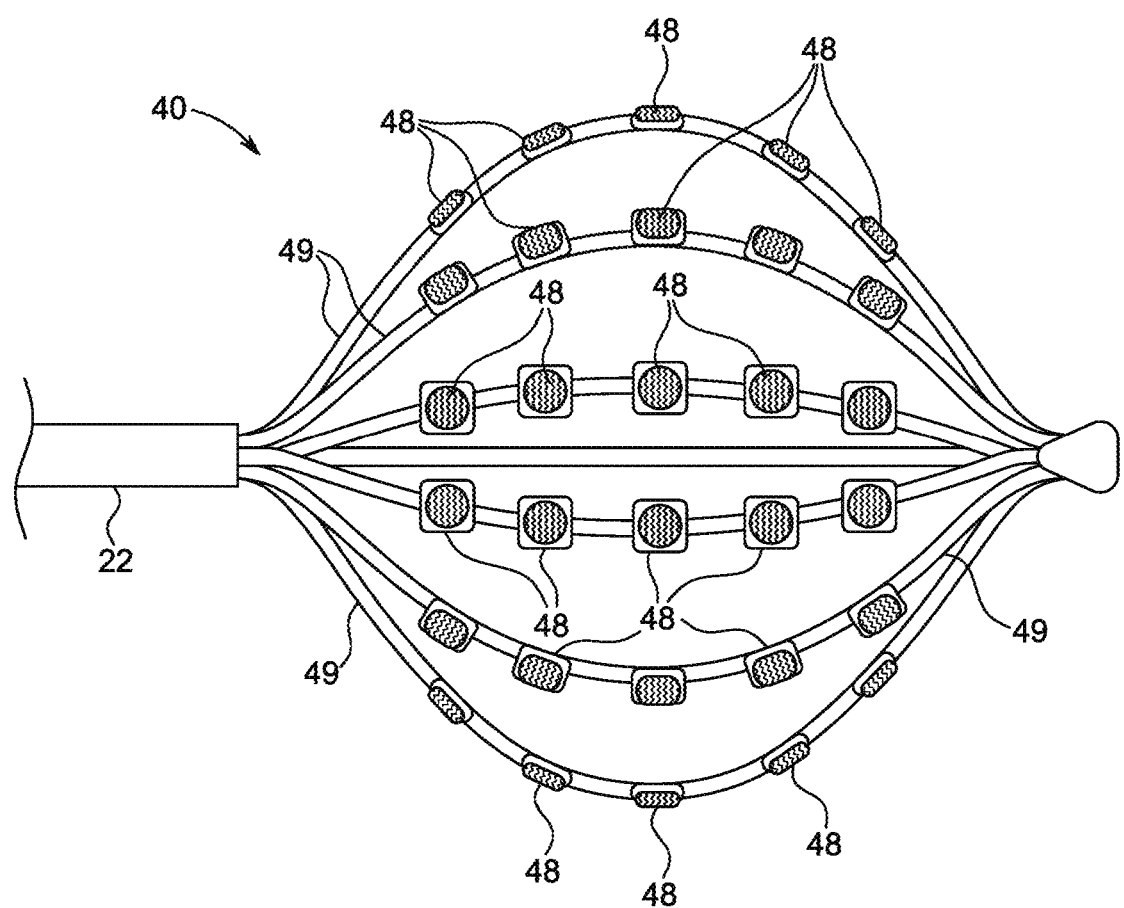
FIG. 2 is an example illustration of a basket catheter with ultrasound transducers.

FIG. 2 is an example diagram of a basket catheter 40 fitted with ultrasound transducers 48, in accordance with an embodiment of the present invention. As shown, the transducers 48 may be coupled to splines 49 and may form a shape, such as a basket. The transducers 48 may be sparsely distributed (e.g., where a large gap may exist between each of two neighboring transducers, such that the majority of surface area of a basket surface defined splines 49 is vacant of transducers). The transducers 48 may distributed in an approximate spherical pattern beyond the distal end of shaft 22. The array of transducers 48 may achieve the required coverage and detail of features of a cardiac chamber despite being sparse because each transducer 48 may have a sufficiently large transmitting and receiving acceptance angle and calculations performed based on signals from and to the transducers 48 may be optimized to utilize sparse arrays, as further disclosed herein.

The catheter 40 shown in FIG. 2 is an example only. The number of transducers 48 and their arrangement may vary. Additional elements, such as electrodes, may be disposed over the splines 49. In one embodiment, there are sixty transducers and the splines are formed as flex PCB splines glued over a nylon balloon. Other catheter geometries (e.g., spiraling arms, balloon, etc.) may be provided.

In one aspect, a device is provided that includes a catheter 40 configured to be inserted into an intra-body cavity of a patient, and an ultrasonic transducer array comprising a plurality of multi-frequency ultrasonic transducers 48 arranged on the catheter 40. Each transducer 48 is configured to transmit a wide beam ultrasonic signal and a narrow beam ultrasonic signal, and each transducer 48 is configured to receive wide beam echo signals and narrow beam echo signals in response to the wide beam ultrasonic signal and the narrow beam ultrasonic signal. The processor 41 is configured to detect free space of the intra-body cavity by processing the wide beam echo signals and the narrow beam echo signals. In one aspect, the processor 41 is configured to detect the free space by determining a bounding reflection value (BRV), and the BRV indicates whether a specific point in space within the intra-body cavity is in the free space. The processor 41 is configured to identify the free space based on at least one of signal directivity or signal intensity, which are described in more detail herein. The monitor or display 27 is configured to illustrate the free space.

In one aspect, the narrow beam ultrasonic signal has a frequency in a range of 12 MHz to 16 MHz, and the wide beam ultrasonic signal has a frequency in a range of 1 MHz to 3 MHz. In one aspect, the wide beam ultrasonic signal has a beam width of at least 40 degrees, and the narrow beam ultrasonic signal has a beam width in a range of 4 degrees to 12 degrees.

A method is also disclosed herein that includes inserting the catheter 40 into an intra-body cavity of a patient. The catheter 40 includes an ultrasonic transducer array including a plurality of multi-frequency ultrasonic transducers 48. The method includes transmitting a wide beam ultrasonic signal and a narrow beam ultrasonic signal from each of the multi-frequency ultrasonic transducers 48, and receiving wide beam echo signals in response to the wide beam ultrasonic signal and narrow beam echo signals in response to the narrow beam ultrasonic signal. The method includes identifying free space of the intra-body cavity by processing the wide beam echo signals and the narrow beam echo signals.

According to an embodiment, a two-dimensional intra-atrial ultrasonic array (e.g., a basket mounted array) may include an ensemble $\Omega$ of N transmitting/receiving elements, as shown in FIG. 2 via the transducers 48. The array may be operated in a synthetic aperture like mode, which includes N transmit-receive events, in which a single element transmits followed by all elements jointly receiving the transmission from the single element. As further disclosed herein, application of such an implementation may result in identifying the locations and reflection coefficients of the scatters at the endocardial surface, where a scatter may occur at points on the endocardial surface.

Each transmitter s may be located at a position $x_s \in R^3$ and may be a source of a spherical pressure wave of the form $Px_s$ (r, t)=$p_0$(t)1/4 Пr $\delta$(r–ct) where r is the distance from the transmitter, c is the velocity of sound in the medium, R is a set of real numbers, and p0 (t) is the signal waveform. As used herein, the term transmitter, transmitter-receiver, or transmitter-receiver pair are all generally used to refer to the transducers.

A wave may be scattered (also referred to as an echo) from a point scatterer sc at $x_{sc}$ and received by a transducer element re at $x_{re}$. An angle $\Theta$(el, X) may be the angle between the normal to the surface of the element el $\in \Omega$ and the vector from the element center to the point X. A Dir($\Theta$, ka) may be the directivity factor which attenuates the signal as a function of $\Theta$, wave number k and element radius a. The signal intensity may be the measured response that is received at a receiver when there is a scatterer at point $x_{sc}$. The signal intensity measured at $x_{re}$. as function of the time t will be:

$$S(s, sc, re) = \frac{cP_1 P_0(s)\delta\left(t - \frac{1}{c}(D(x_s, x_{sc}) + D(x_{sc}, x_{re}))\right) Dir(\Theta_{s,sc}, ka) Dir(\Theta_{sc,rc}, ka)}{16\pi^2 D(x_{re}, x_{sc}) D(x_s, x_{sc})}.$$

(Equation 1)

In the above equation, $P_0$(s) is the peak envelope ((the absolute value) of the complex envelope) of the signal transmitted from s, P1 is the scattering coefficient of the scatterer at sc, c is the speed of sound in the medium and D (x, y)=∥x–y∥ denotes the Euclidian distance between the two points x and y.

For a transmitter-receiver pair s, re$\in \Omega$ at $x_s \in R^3$ and $x_{re} \in R^3$, respectively, all points $x_{sc} \in R^3$ satisfying the equation $c \cdot t_{s,sc,re}$=D($x_s$, $x_{sc}$)+D ($x_{sc}$, $x_{re}$), define an ellipsoid E$\in R^3$ such that its two foci s and re lie on its major axis of length $c \cdot t_{s,sc,re}$.

Based on experimentation, as further disclosed herein, it has been shown that all signals transmitted from $x_s$ and scattered from all scatterers sc$\in$ E (s, re, sc) will be received at $x_{re}$ simultaneously and coherently.

Further, the maximum signal envelope S (s, re, sc) transmitted from s and received at re after $t_{s,re,sc}$ seconds, having been scattered from all reflectors sc$\in$ E (s, re, sc) is given by the following integration:

$$S(s, re, sc) = \oint_{X \in E(s,re,t_{sc})} \frac{P_1(X) P_0(s) Dir(\Theta_{s,sc}, ka) Dir(\Theta_{sc,re}, ka) dX}{16\pi^2 D(x_{re}, x_{sc}) D(x_s, x_{sc})},$$

(Equation 2)

In the above equation, $P_0$(s) is the maximum of the envelope of the signal transmitted from s, assumed to be positive and s independent and $P_1$(X) is the reflection coefficient at X. Equation 2 provides the signal intensity based on all scatterers that lie over a given ellipsoid such that the signal intensity value provided by Equation 2 may correspond to the actually measured signal intensity at a receiver at a given time.

According to embodiments disclosed herein, the free space is the ensemble F of all points X, for which $P_1$(X)=0. Any area that includes a blood pool would exhibit minimal reflectance such that after a bounding reflection value, as further described herein, is calculated, a segmentation technique may be applied to remove such blood pool regions from the calculation of a surface. The segmentation technique may be applied over the BRV to detect free space (e.g., blood pool regions) from the calculation of a surface, as further provided herein.

Regarding the BRV, the disclosed subject matter provides the ability to integrate different beam patterns (i.e. directivity) to achieve imaging and detection of openings or holes (i.e. pulmonary veins) by using narrow beams, and a better view of the shape using beams of differing widths. Certain aspects of imaging techniques are generally disclosed in US Patent Pub. 2019/0209089, which is incorporated by reference as if fully set forth herein. Generally, the BRV examines a set of time shift signals, but focuses on the minimum of the envelope (i.e. energy) of all the signals in the appropriate time instead of calculating a summation, which is used in the ellipsoidal back projection technique. The principles of the BRV are based on the concept that if even one transducer/transmitter-receiver pair receives no echo (i.e. noise level signal) at a specific time, then all the points with the corresponding time-of flight (i.e. from the transducer to the point in space, and back to the receiver) are in free space.

The segmentation technique may be any applicable technique, e.g. region growing, such that it distinguishes blood pools which have low signal intensity values from surfaces which have high signal intensity values. Given that the entire group of transducer elements $\Omega$ is in the free space and since the acoustic impedance of myocardial tissue is larger than that of blood, it follows that for all scatterers $P_1$(X)≥0. The triplets (s, re, sc); sc$\in$ E (s, re, sc); and s, re$\in \Omega$ define all ellipsoids passing through the point sc whose foci are all transducer elements in $\Omega$. Given the above, since the integrand in Equation 1 is non-negative, it follows that if S (s, re, sc)=0, then $P1(x_{sc})$=0 such that sc E F where the point sc is in the free space.

Figure 3:
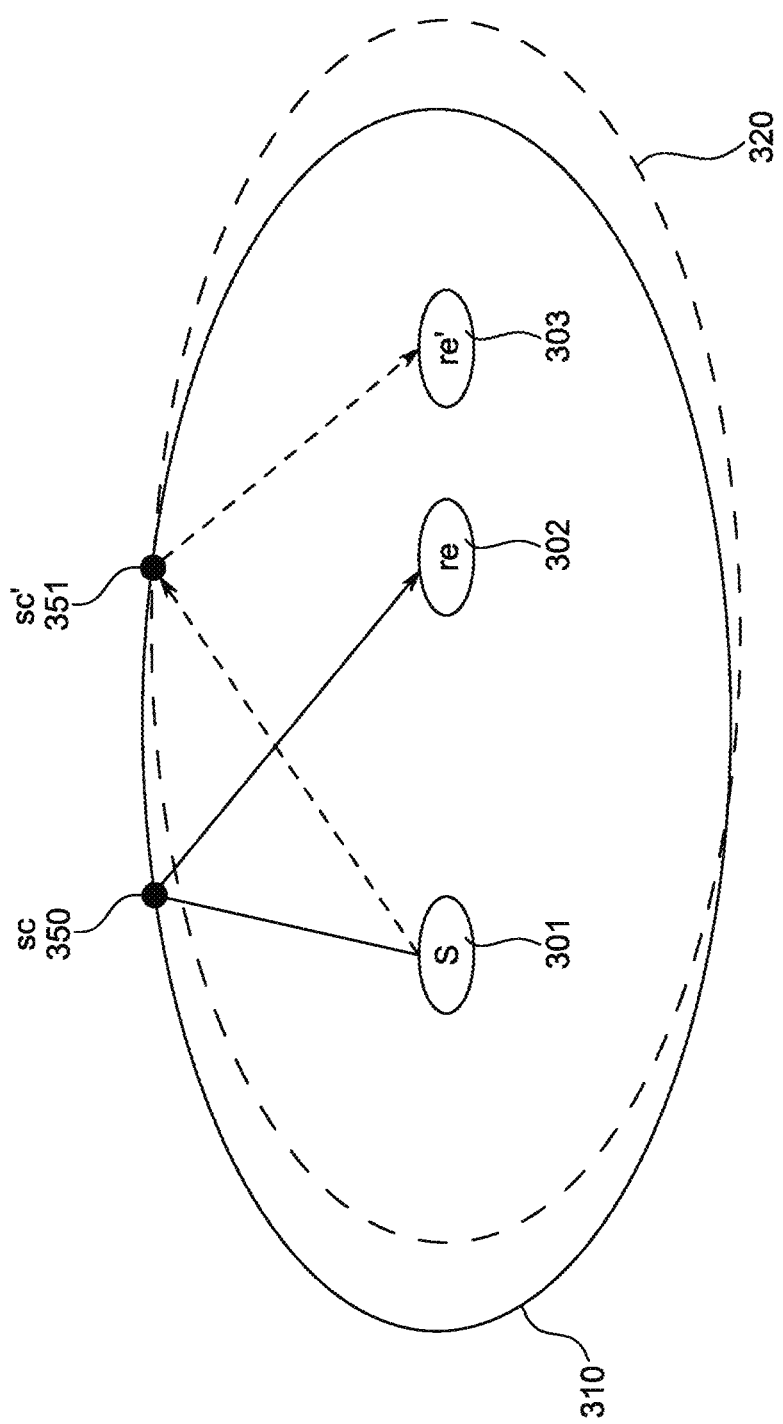
FIG. 3 is an example diagram of a projection mapping technique.

FIG. 3 shows an example illustration of the elliptic Radon-like projection where the point sc 350 is an actual scattering element while sc' 351 is in the free space. The two ellipses 310 and 320 induced by pairs (s 301, re 302), (s 301, re' 303) intersect at sc' 351 but not sc 350.

Equation 3 below accounts for the distance and directivity at a specific point:

(Equation 3)

$$\hat{S}(X, s, re) = \frac{S(X, s, re) 16\pi^2 D(x_{re}, x_{sc}) D(x_s, x_{sc})}{P_0(s) Dir(\Theta_{s,sc}, ka) Dir(\Theta_{sc,re}, ka)}$$

In Equation 3, when s, re$\in \Omega$, then $P_1(X) \leq \hat{S}$, for all X, s, re.

The BRV may be defined for all points X as:

$$\rho(X) = \min_{s,re|X \in E(s,re,sc); s,re \in \Omega} \hat{S}(X, s, re). \quad \text{(Equation 4)}$$

As defined above, the BRV is measured in A/D voltage, which is proportional to the received wave acoustic pressure. The BRV may be computed by segments of volume, e.g. detected free space. For example, the BRV may be computed by segmenting a volume (10 cm)$^3$ centered in the middle of a catheter (e.g., a basket catheter) and sampled using a three-dimensional 2 mm grid. The volume may be segmented into a connected free space by using a region growing algorithm (e.g., Equation 2) with a seed at the volume center. The voxels at the perimeter of the resulting free space may also be referred to as the detected boundary points.

In other words, the BRV is computed in a voxel grid in space to produce a 3D image, similar to a CT or MRI. This image is used to segment the space of interest into free space and tissue, which gives a set of points on the boundary that represent the chamber surface. These can be later processed using additional advanced algorithms, such as model based fast anatomical mapping (mFAM) or smoothing methods or neural networks to produce a realistic looking surface image.

The BRV gives low values (i.e. noise values) for locations in the blood pool, which are always free, and higher values (i.e. at least a single scatterer $P_1$) for potentially occupied locations. These values will vary due to relative distances, directivity, etc. The values are also impacted by system parameters that influence the signal to noise ratio (i.e. frequency voltage, amount of averaging, filtering, etc.), and the reflecting tissue itself. In certain applications, the signal to noise ratio (SNR) can be 10, i.e. the signal is around 500-1000 while the noise levels are less than 100.

The left atrial boundary is determined by starting from a volume of 10*10*10 cm 3 centered in a middle of the catheter, and sampled using a 3-D grid having a voxel resolution of 2*2*2 mm$^3$. In one embodiment, the BRV is first computed for every voxel in the volume. Then, in one embodiment, the volume is segmented into a connected free space using a region growing algorithm with a seed at the volume center. A growing zone algorithm is used to define a locally adaptive threshold for the BRV. Where the region is below a predetermined threshold, that particular region is deemed to be free space. The voxels at a perimeter of the resulting free space are referred to as the detected boundary points.

Embodiments of the disclosed subject matter may utilize both wide beams and narrow beams to map an intra-body chamber. Each element may be configured to transmit both the wide beams and the narrow beams, and to receive corresponding wide beams and narrow beams. The wide beams may have a first directivity or be within a range of first directivities and the narrow beams may have a second directivity or be within a range of second directivities. The narrow beams may be used in addition to the wide beams as the wide beams may be too wide to distinguish between holes (e.g., pulmonary veins (PVs)) and an intra-body chamber surface (e.g., an endocardial surface), as may be the case for an absence of an ellipsoid that is entirely in free space that intersects the interior of the PV.

At a general level, the free space method essentially includes using a highly sparse array of ultrasonic elements, i.e. the catheter 40 and the transducers 48, to transmit signals, and then determine, based on the echoes or reflected signals, whether the transducers are in free space (i.e. in blood or not touching a heart structure) or occupied space (i.e. touching a heart structure). The wide beam echo signals will have one set of characteristics and the narrow beam echo signals will have another set of characteristics.

The free space method combines extended non-linear beamforming and surface rendering. An analytic scheme is provided to determine the number of array elements and frequencies required to achieve a desired segmentation accuracy. The catheter 40 disclosed herein captures hundreds of surface points or scans simultaneously. Each scan takes less than 16 ms, in the case of using three frequencies, which provides for real time tracking of the endocardial surface. The boundary, which represents the chamber surface, is determined by segmenting the BRV that was sampled in the voxel grid using a region growing algorithm. The boundary can be tracked in time to provide real-time movement imaging.

Additional information about the free space may be acquired using a dependence of the emitter directivity pattern as function of the wavelength. Based on this configuration, it is possible to use both narrow and wide beams to map or identify regions of the cavity that may be smaller than the main chamber. The directivity for a piston model is proportional to:

$$Dir(\Theta, ka) \propto \frac{2J_1(ka\sin\Theta)}{ka\sin\Theta} \quad \text{(Equation 5)}$$

In Equation 5, $J_1$ is the first order Bessel function. A directivity can either produce wide beams suitable for an ellipsoidal back projection or narrow beams which provide a laser like scan into a narrow portion of an intra-body cavity (e.g., a PV). Beams with interim width may add information to the ellipsoidal back projection.

Figure 4B:
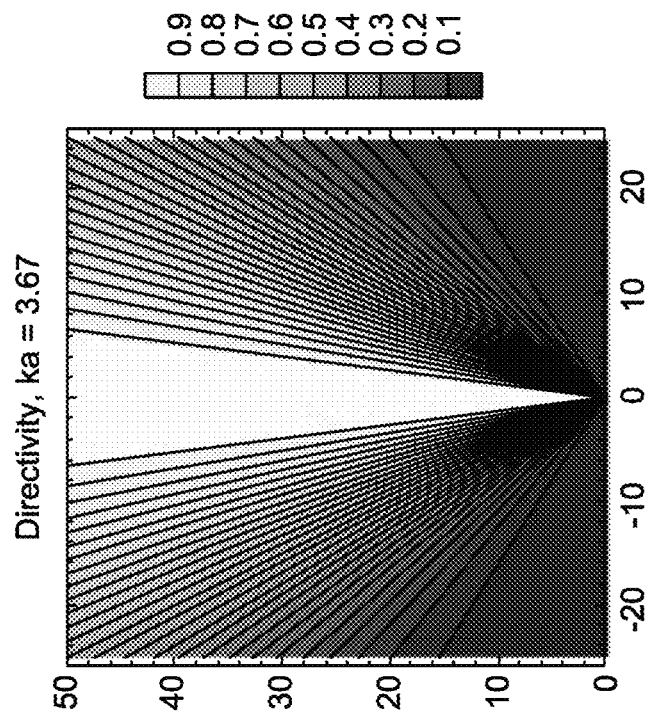
FIG. 4B is a graph of an example wide beam pattern.
Figure 4A:
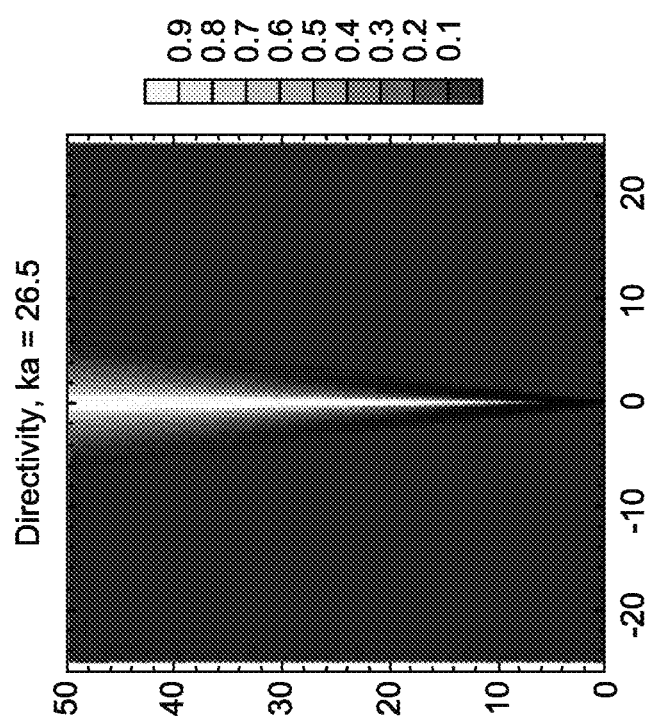
FIG. 4A is a graph of an example narrow beam pattern.

FIG. 4A shows an example of a narrow beam (at 13 MHz) pattern with a directivity, ka, of 26.5. FIG. 4B shows an example of a wide beam (at 1.8 MHz) pattern with a directivity, ka, of 3.67. A normalized intensity value is shown on the right-hand side of these figures. The narrow beams may be used in first echo detection mode such that a given space is free until it hits the first echo. The response information from transmission and receipt of such narrow beams is added to the wide beam scan to obtain mapping information for narrow portions of an intra-cardiac chamber such as a vein (e.g., PV).

In one aspect, the narrow beams are used in a first echo mode. The system then checks for the first time when the signal is above a noise level threshold, and sets this instance or time as a hit. The time corresponds to a distance. The transducer location, orientation, and beam shape are all known variables. Regarding the beam shape, it is assumed that the beam is a narrow cone with a known angle, which is computed using the directivity (i.e. the angle is defined to be from the center until there is 6 DB down, which is about 10 degrees for 13 MHz). All the space in the cone from the transducer until the hit occurs is considered free, while a region around the hit is occupied. This information is added to the segmented map, where the free space detected by the narrow beams is given higher precedence over the wide beams. In other words, a space considered occupied by the wide beams and free by the narrow beams is ultimately determined to be free. This accounts for mapping various smaller pathways or veins to and from the chamber.

Beam directivity depends on wavelength. Shorter wavelengths emit narrower beams, while longer wavelengths emit wider beams. Based on this configuration, additional information is gained or determined because wide beams are generally insufficient to detect holes (i.e. pulmonary vein ostia) in the endocardial surface, which would require the ellipsoid to exist in a fully contained free space. Using the techniques disclosed herein, points in space are disregard in which the directivity attenuates more than 6 DB for either the transmitter or the receiver, and therefore there is a negligible contribution to the signal. Varying the beam widths continuously between beams directed to the ellipsoidal method to narrow beams, which provide a laser-like scan into the pulmonary vein provides an improved image. Beams having an intermediate or interim width compared to the wide and narrow beams may also be used to provide additional information.

Figure 5:
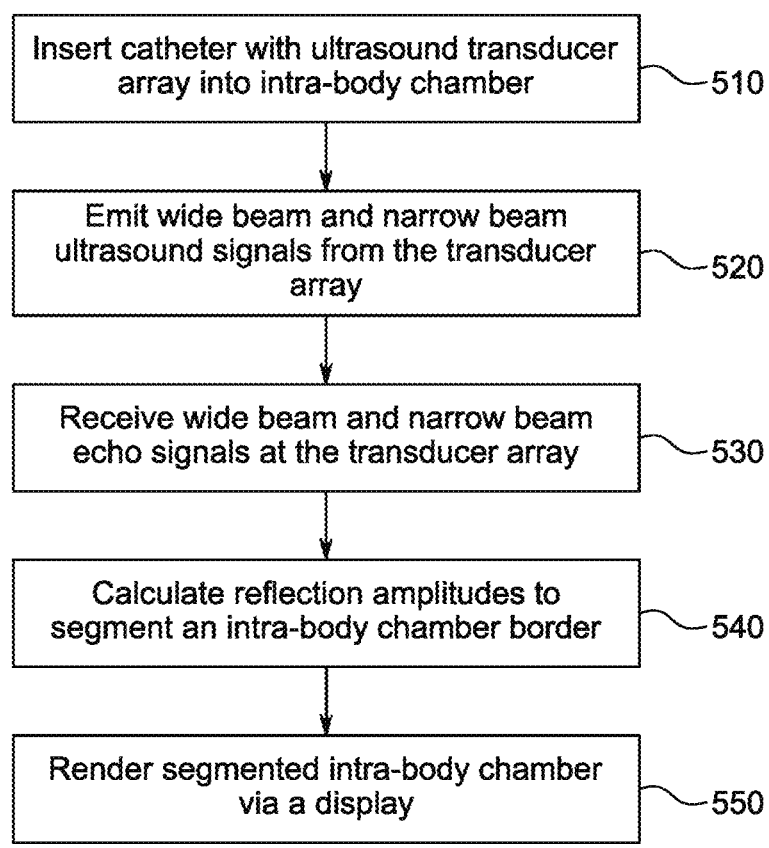
FIG. 5 is flowchart for mapping an intra-body chamber.

FIG. 5 shows flowchart 500 for mapping an intra-body chamber in accordance with the embodiments disclosed herein. As shown, at step 510, a catheter that includes an ultrasound transducer array (e.g., basket catheter 40 of FIG. 2) is inserted into a patient's body. The ultrasound transducer array is inserted into an intra-body chamber such as a cardiac chamber. At step 520, the transducers within the ultrasound transducer array transmit wide beam and narrow beam echo signals. At step 530, the echo signals are received at one or more transducers within the ultrasound transducer array after being reflected off of free space scatterers and actual scatterers, which include major myocardium surfaces as well as narrower surfaces such as veins (e.g., pulmonary veins).

At step 540 of flow chart 500, a processor calculates reflection amplitudes to segment an intra-body chamber (e.g., endocardial) border, based on the techniques disclosed herein. In one aspect, a processor is configured to combine multiple scans during catheter movement. Using these scans, a model based fast anatomical mapping (mFAM) can be created by matching a statistical model to data collected by the catheter. In one aspect, a combination of imaging techniques is used in which free space takes precedence over occupied space. In one aspect, a minimum operator is used over the BRV values from all scans, for every point in space of the sampled grid. A region growing algorithm is used to provide boundary voxels between the free space and the chamber tissue. To further improve this imaging technique, an anatomically aware algorithm, such as the mFam or a neural network imaging tool can be used.

At step 550, the segmented intra-body chamber is rendered via a display. A display, monitor, or other type of output device can be configured to receive and display the segmented intrabody chamber data.

Figure 6A:
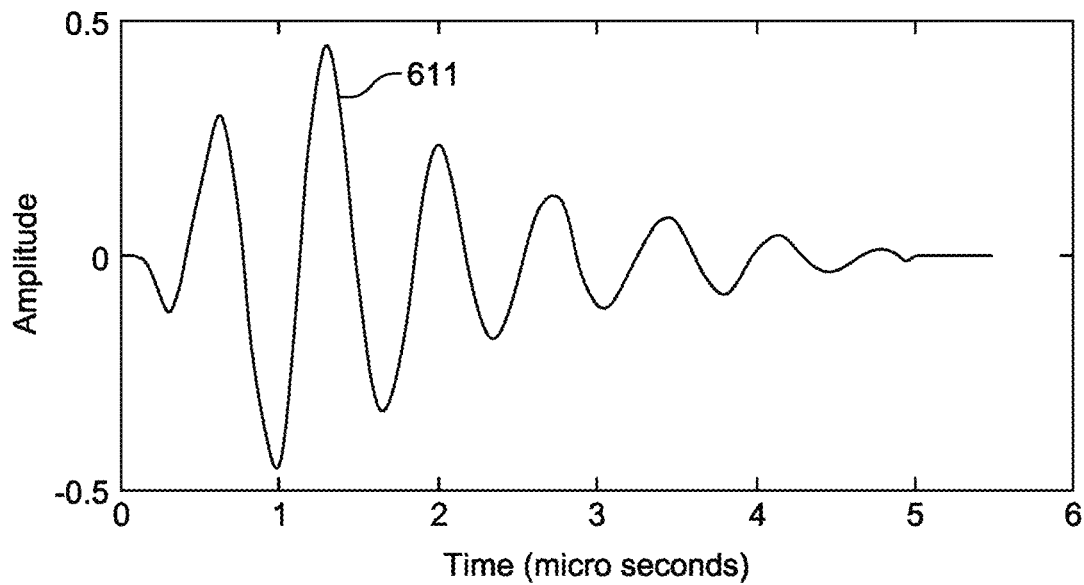
FIG. 6A is a graph of an example wide beam 1.6 MHz simulated signal template.
Figure 6B:
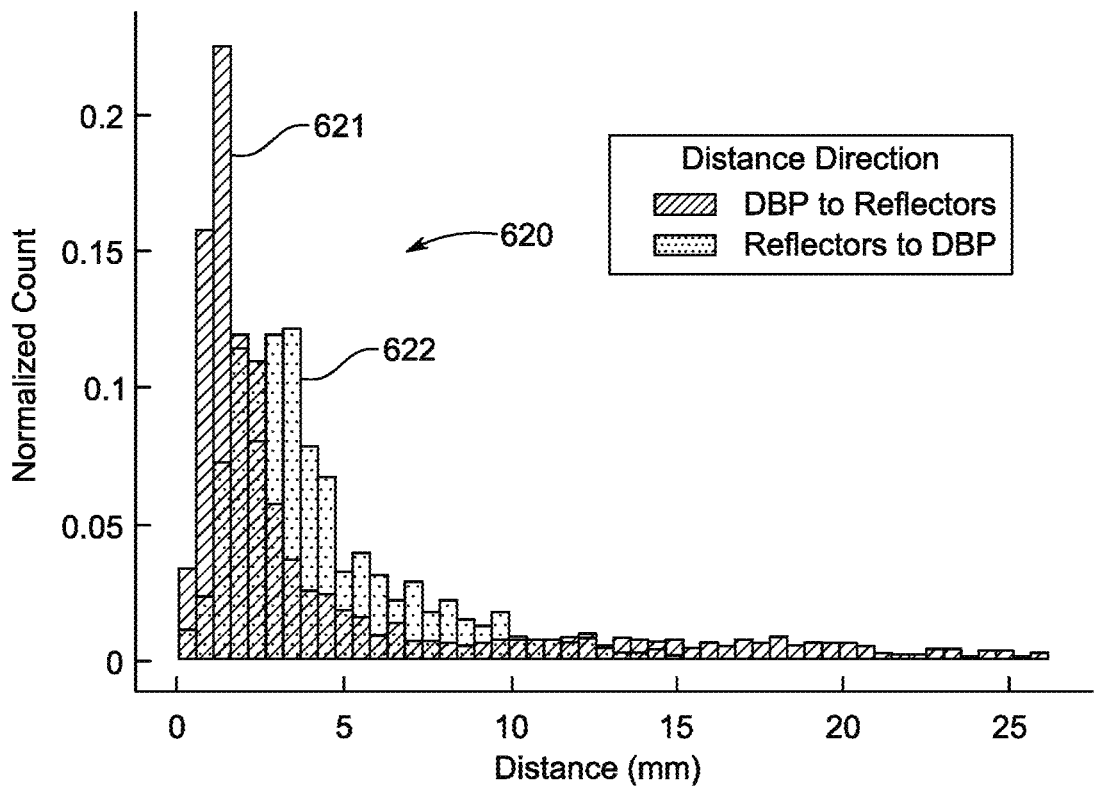
FIG. 6B is an example graph that shows distances between detected boundary and simulated reflectors.

According to an in-silico experiment, a 64-element transducer with a radius of 30 mm radius was inserted into a left atrial model and placed at the center of a 10 cm side cube. The cube was divided into 50³ voxels using a 2 mm three-dimensional grid. A reflector was assigned to all grid points inside a 6 mm thick shell about an atrial boundary of a cardiac chamber. Signals 611 of a several cycles of 1.6 MHz and 7.4 MHz sine function with a Gaussian envelope, as seen in chart 610 of FIG. 6A were assumed. For each transducer element pair, the response for each reflector was appropriately time shifted and summed generating a simulated signal according to Equation 1. The simulated signal was used to reconstruct volumes of wide and narrow responses in accordance with the embodiments disclosed herein. Distances between detected boundary and simulated reflectors are shown in the graph 620 of FIG. 6B, which describes two-sided normalized distance probability. As the distributions are skewed, the median and median absolute deviation (MAD) of the distances (in mm), resulted in 1.99 and 0.983, respectively, for the detected boundary to reflectors 621 and 3.377 and 1.26, respectively, for the reflectors to boundary 622. The distances for the detected boundary to the reflectors and the reflectors to the boundary estimate the error from the surface of the model.

Figure 7:
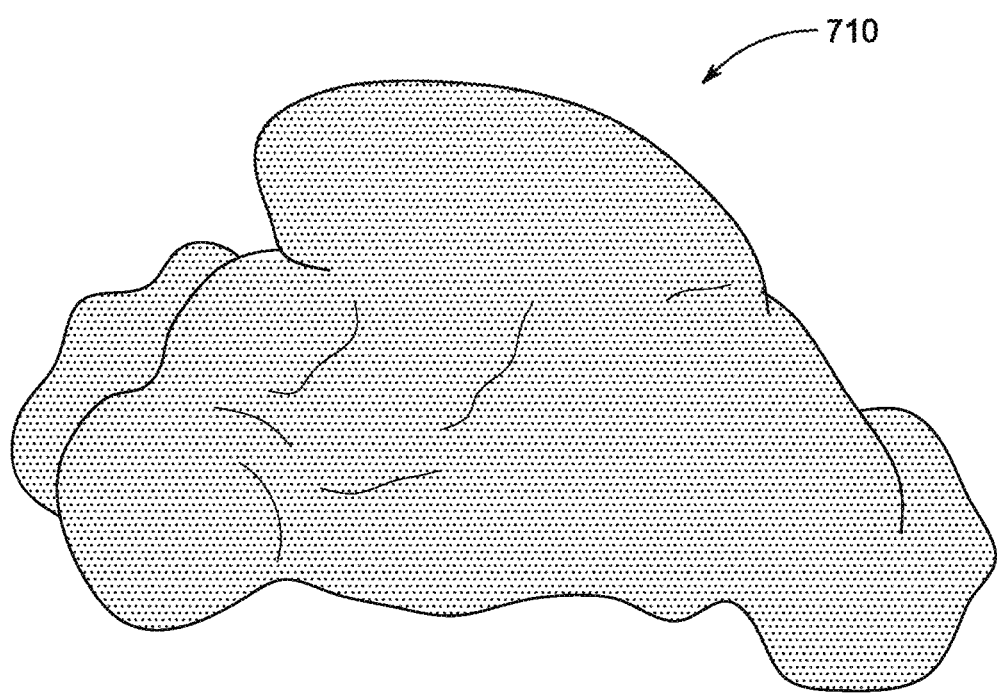
FIG. 7 is an example left atrium silicon phantom.

According to an in-vitro experiment, a 64-element piezoelectric transducer array mounted on a twelve printed circuit board (PCB) splines basket was tested. Each transducer element included two resonance frequencies at about 1.6 MHz and 7.4 MHz, respectively. The elements were connected to an acquisition system capable of generating pulses and recording a sweep of sequential transmissions for all elements in real time. The catheter was placed in a phantom chamber that included a water bath to simulate blood, and was enclosed in an ellipsoidal plastic enclosure, simulating the walls of a cardiac chamber. The walls of the phantom chamber were forced to move continuously by pumping water in and out, in order to simulate a natural cardiac wall-motion. Long time averages were then subtracted from all temporal signals in order to eliminate the constant signals caused by the reflections from the splines themselves. In all simulations, the locations of the transducers were assumed to be known. FIG. 7 shows an example left atrium silicon phantom which may be used to test the embodiments disclosed herein.

Figure 8A:
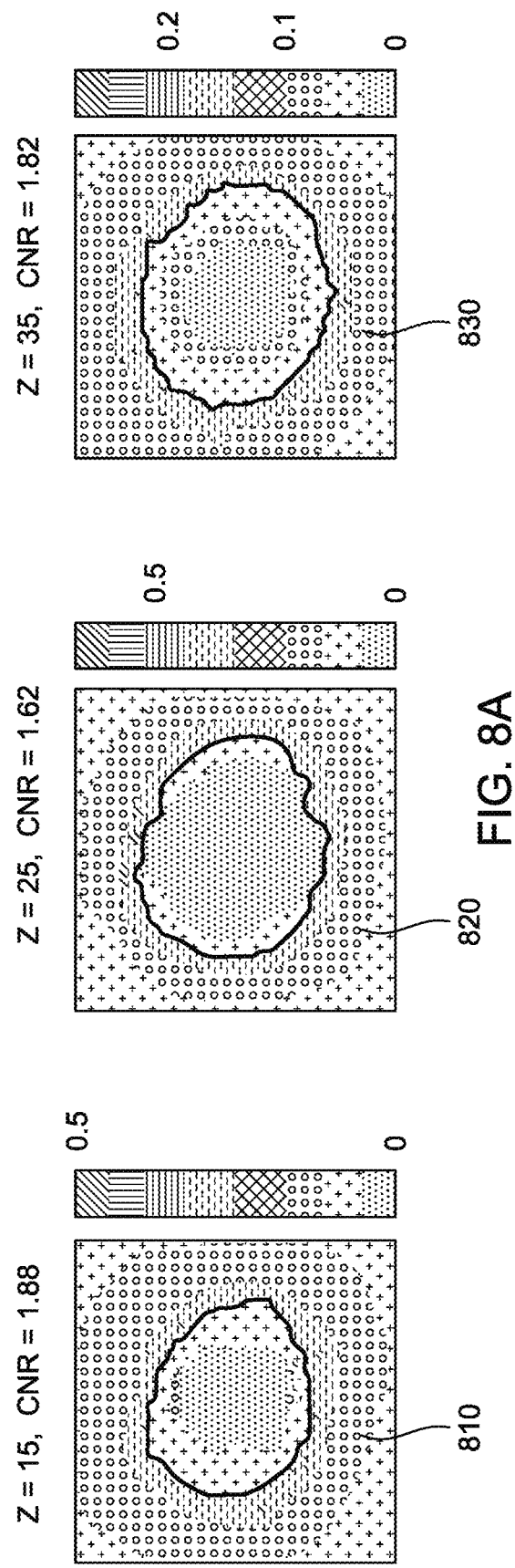
FIG. 8A shows example slices of recorded volume with contrast to noise ratio (CNR).

According to an ellipsoidal phantom experiment, a basket catheter was placed in an ellipsoidal shaped phantom, having radii of 35 mm, 32.5 mm, and 22.5 mm, made of silicon water. Acquisition was performed using wide beams, as described herein. The volume underwent dynamic range reduction using a square root function such that each acquired voxel in the given volume was square rooted. An ellipsoid was fit to the boundary detected by the algorithm. FIG. 8A shows slices of recorded volume with contrast to noise ratio (CNR) computed for pixel populations at 6 mm around the boundary. Element 810 shows a CNR of 1.88 with a Z value (slice along height axis) of 15, element 820 shows a CNR of 1.62 with a Z value of 25, and element 830 shows a CNR of 1.82 with a Z value of 35. The values on the right-hand side of FIG. 8A are the intensity values.

Figure 8B:
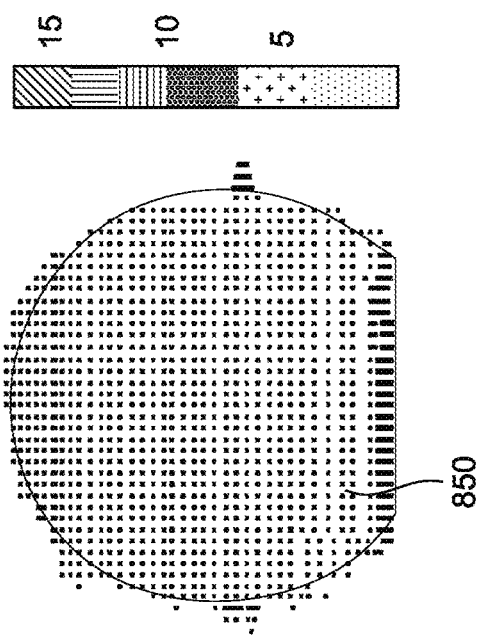
FIG. 8B shows an example fitting of an ellipsoid to detected boundary data.

FIG. 8B illustrates the fit and deviations of the detected boundary. A distance value in mm is shown on the right-hand side of FIG. 8B. As shown, an ellipsoid 850 is fitted to the detected boundary data. Only the frontal half of the volume is shown in FIG. 8B. The bottom portion of the fit and deviations, as shown in the ellipsoid 850 of FIG. 8B, is an outlier as the phantom used for this experiment was not a complete ellipsoid. Accordingly, the bottom portion skews the error distribution, median and MAD (which estimates standard deviation in a Gaussian distribution with a factor of around 1.5). The radii obtained based on this experiment were 36, 33.4 and 25.5, while the ellipsoid median deviation from the data was 1.4 mm and MAD is 0.6283 mm.

Figure 9:
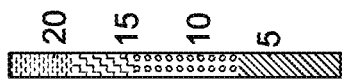
FIG. 9 illustrates reconstruction data regarding left atrium phantom modeling.
Figure 9:
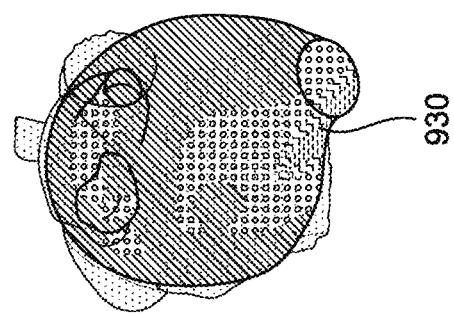
Figure 9:
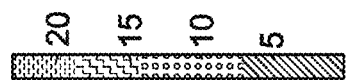
Figure 9:
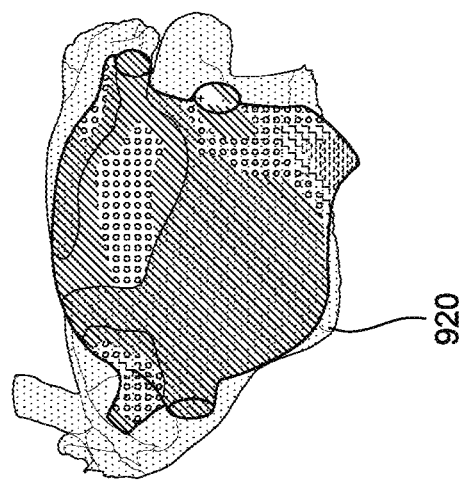
Figure 9:
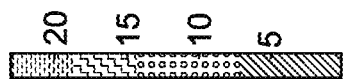
Figure 9:
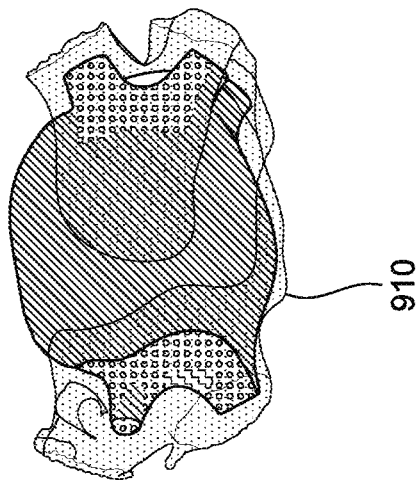

According to a left atrium phantom experiment, a silicon left atrium phantom, as shown in FIG. 7, was scanned using narrow and wide beams. The detected boundary points, along with six manually tagged points of anatomical interest were used as input to an anatomically aware, model-based reconstruction algorithm. The reconstructed anatomy was aligned with a ground truth CAD mesh and the difference from each vertex of the reconstruction to the ground truth mesh was calculated. The resulting mean, standard deviation, median, MAD and RMS were 4.2 mm, 4.4 mm, 2.6 mm, 1.77 mm, 6.1 mm, respectively. Reconstruction result and error are shown in FIG. 9. As shown in FIG. 9, the right-hand side indicates distance in mm. Element 910 of FIG. 9 shows a top view of the detected boundary-based model to atrium phantom distances, in millimeters. Element 920 of FIG. 9 shows a side view of the detected boundary-based model to atrium phantom distances, in millimeters. Element 930 of FIG. 9 shows a left PV view of the detected boundary-based model to atrium phantom distances, in millimeters. As shown, the resulting model is visually close to the phantom, while the detected PVs are consistent with the CAD. In a left atrial shaped silicon phantom, the images are accurate to within at least 4.0 mm using the systems, apparatuses, and methods disclosed herein.

In one aspect, the array is operated in a synthetic aperture mode, including a number (N) of transmit-receive events. In this mode, each element in the array sequentially transmits once, while all of the elements receive. An ensemble is generated that includes (N(N+1))/2 distinct RF signals. According to the embodiments disclosed herein, locations and reflection coefficients $P1(x_{sc})$ of the scatterers $x_{sc}$ are located and found at the endocardial surface boundary using this ensemble of signals. In one aspect, all of the signals in the ensemble are sampled, which are used to define a specific location in space. In other words, if one of the signals receives no echo from a particular location, then it is determined or assumed that there is free space in that region. If a low value signal is generated, then it is determined or assumed that the catheter is positioned in blood.

Figure 18A:
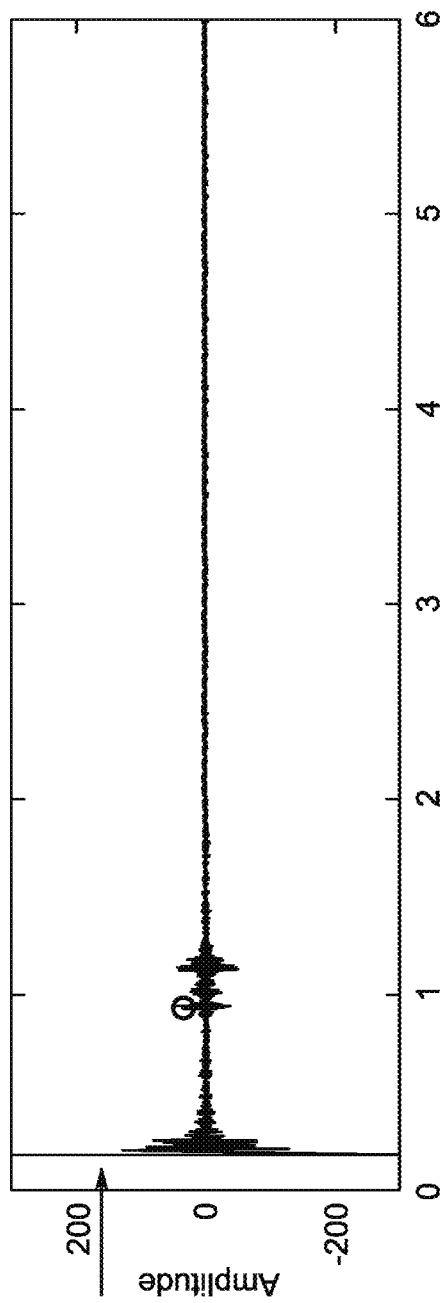
FIGS. 18A and 18B illustrate a response for a high frequency signal from a transducer.
Figure 18B:
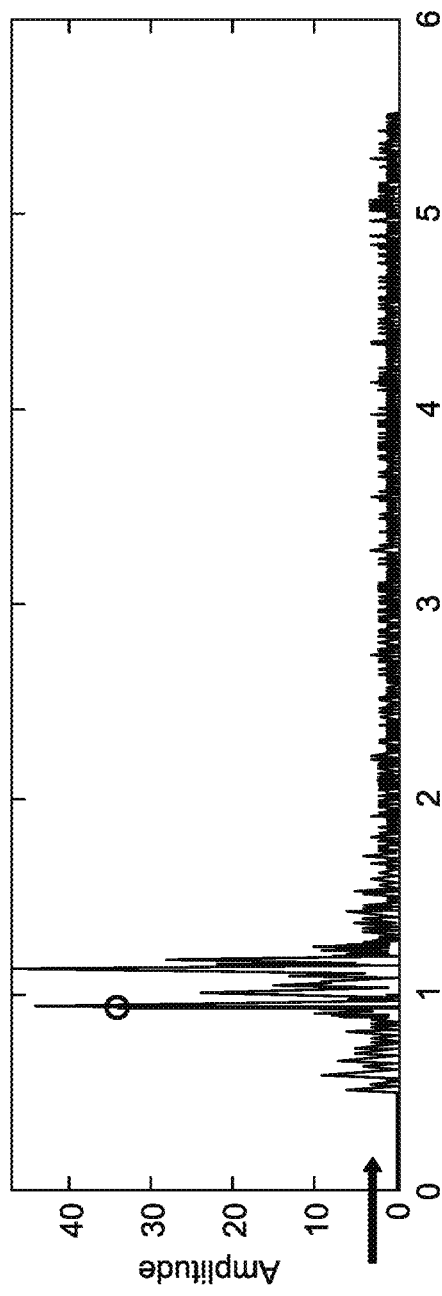

A chart is generated with the signal amplitude versus distance. As shown in FIGS. 18A and 18B, an RF response for a high frequency signal from a transducer is measured. FIG. 18A indicates an RF response after applying a median filter on fifteen signals. The arrow in FIG. 18A indicates an excitation signal. FIG. 18B illustrates an absolute value for the amplitude with the excitation signal removed. The circled portion in FIG. 18B indicates a first hit, and the arrow indicates a dead zone.

A signal emitted from a transducer element at $x_s$ reflected from a point reflector at $x_{sc}$ with a reflection coefficient $P1(x_{sc})$ is received at $x_{re}$ after a time td, which is defined in Equation 6 below:

$$t_d(s, re, sc) = \frac{1}{c}(\|x_s - x_{sc}\| + \|x_{sc} - x_{re}\|) \quad \text{(Equation 6)}$$

In Equation 6, c=1.54 mm/µs, which is the speed of sound in blood, and is a $t_d$(s, re, sc) delayed copy of:

$$\phi(s, re, t) = P_0 e^{\frac{-(t)^2}{\tau^2}} e^{-i\omega t} \quad \text{(Equation 7)}$$

In Equation 7, $P_0$ is the transmission/reception peak amplitude corrected by transmit and receive directivities defined by Equation 8 below:

$$Dir(\Theta, ka) = \frac{2 J_1(ka\sin\theta)}{ka\sin\theta} \quad \text{(Equation 8)}$$

Equation 8 corresponds to a directivity factor which attenuates the signal as a function of incidence angle with the transducer surface $\Theta$. In Equation 8, the wave number k=(2 πf/c), $J_1$ is a first order Bessel function, and the element size a=0.5 mm. Per Equation 8, these values are divided by the transmitter scatterer and receiver distances, and are multiplied by the scattering coefficient $P_1(x_{sc})$.

Image system quality is generally measured by a response to a single point reflector. In one aspect, the response to the reflector is a point spread function (PSF). In one experiment, point spherical reflectors were placed in front of a planar rectangular array with nine elements. Array-to-reflector distance was four to five times the distance between the individual array elements. FIGS. 10A-10F compare the PSF and two reflector response for the free space (FS) and envelope and coherent summation (DAS) methods. The values on the right-hand side of FIGS. 10A-10F indicate intensity values.

Figure 10A:
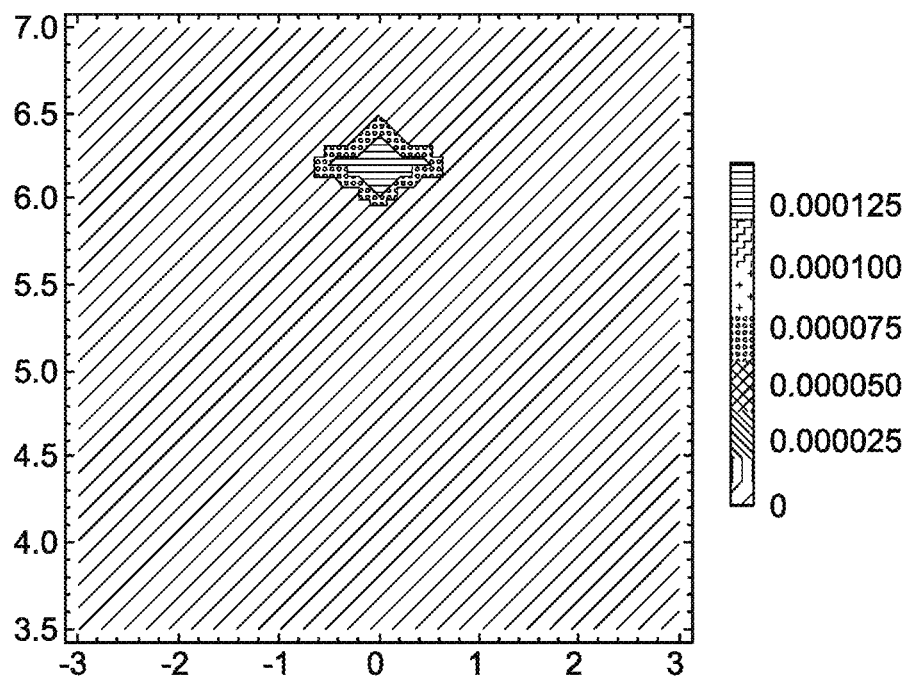
FIG. 10A illustrates a model created by free space mapping using a single reflector.
Figure 10B:
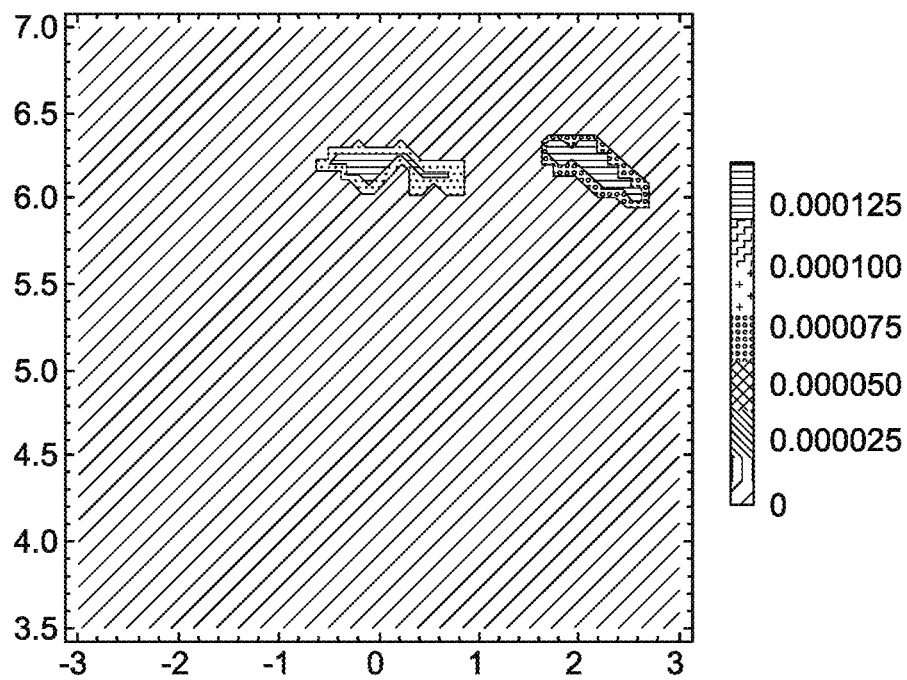
FIG. 10B illustrates a model created by free space mapping using a double reflector.
Figure 10C:
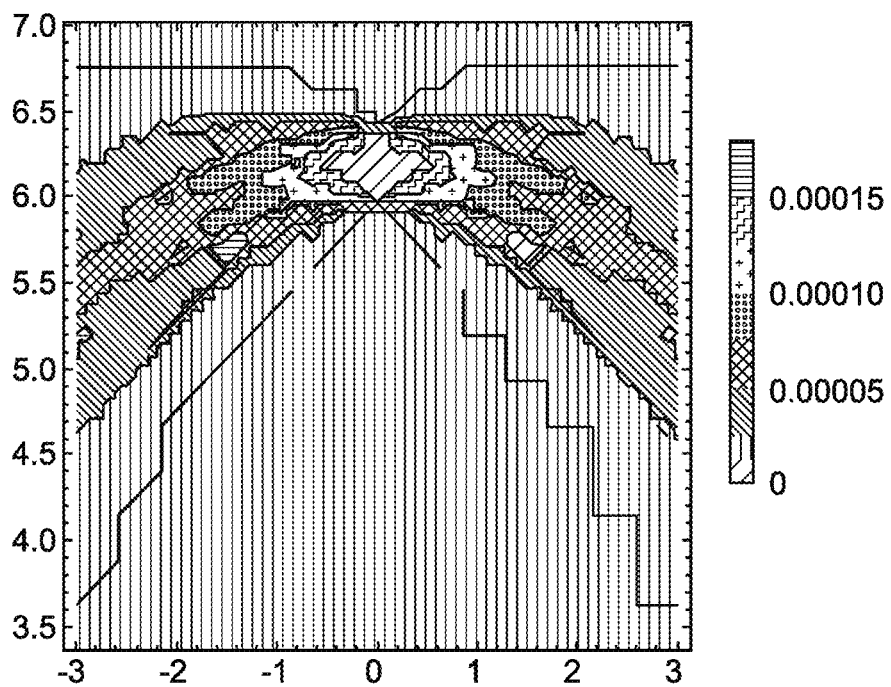
FIG. 10C illustrates a mean absolute summary mapping using a single reflector.
Figure 10D:
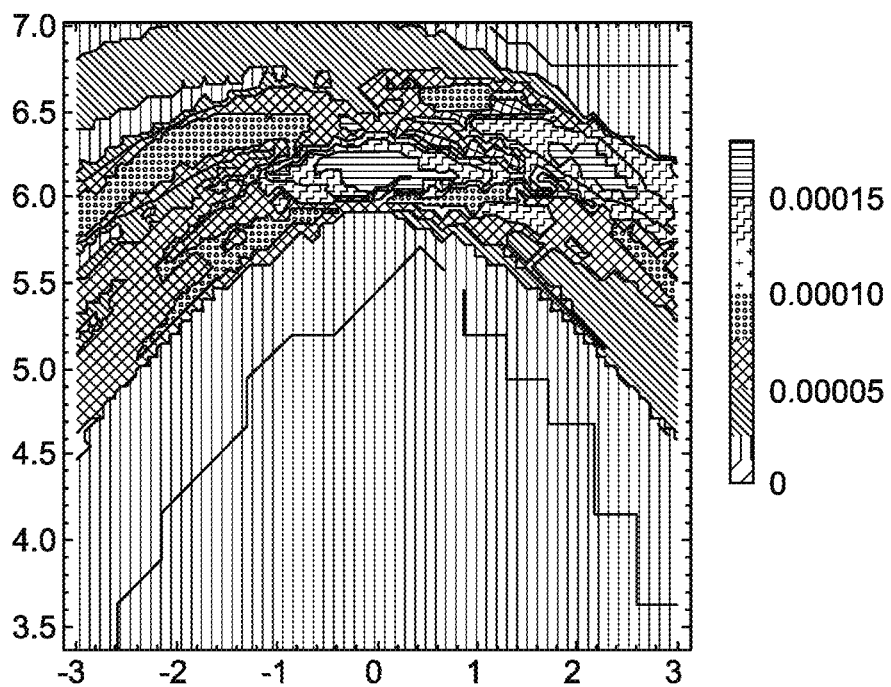
FIG. 10D illustrates a mean absolute summary mapping using a double reflector.
Figure 10E:
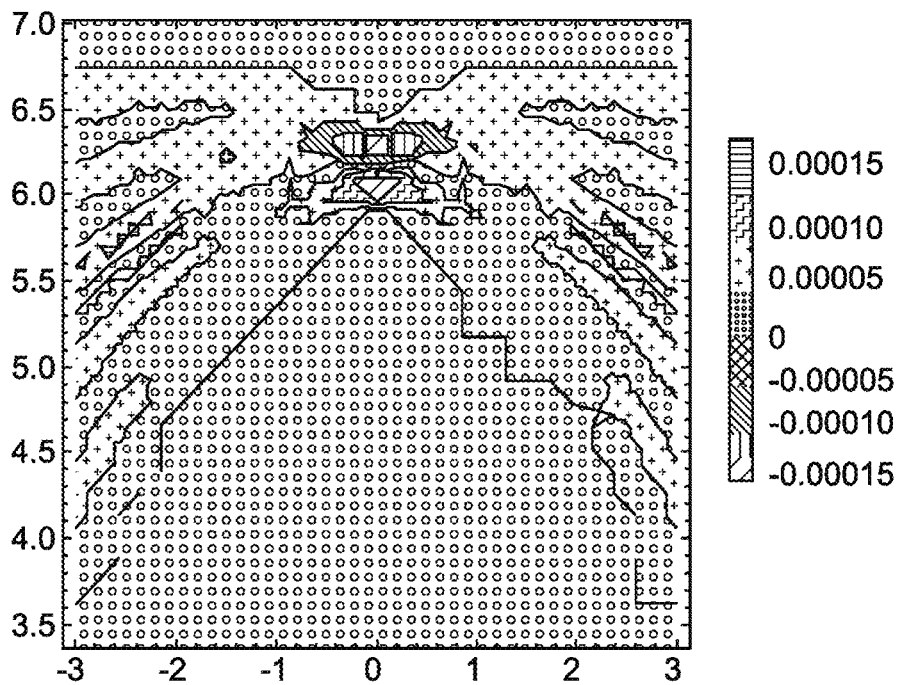
FIG. 10E illustrates a coherent sum mapping using a single reflector.
Figure 10F:
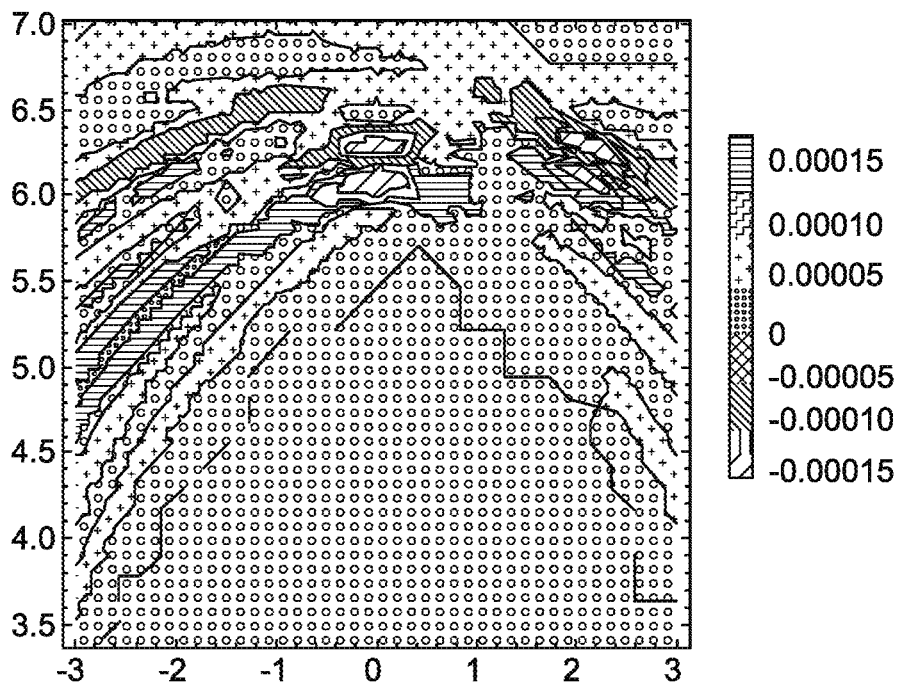
FIG. 10F illustrates a coherent sum mapping using a double reflector.

FIGS. 10A and 10B correspond to a free space mapping, FIGS. 10C and 10D correspond to a mean absolute summary mapping, and FIGS. 10E and 10F correspond to a coherent sum mapping. FIGS. 10A, 10C, and 10E correspond to a single reflector arrangement, and FIGS. 10B, 10D, and 10F correspond to double reflector arrangement. As shown in FIGS. 10A and 10B, the free space method has a PSF with minimal array processing artifacts and distinguishes between the two reflectors. As shown in FIGS. 10C-10F, DAS experiences up to 33% of the reflector signal across the space, and DAS also experiences up to 40% blurring between the two reflectors. If the element's position accuracy is less than a sub-wavelength for a non-rigid catheter, then only the absolute value summation is feasible and causes relatively larger artifacts. In other words, it is assumed that the left atrium and other chambers are bodies that can be closely approximated as an ellipsoid. Accordingly, this assumption provides a relatively accurate approximation of actual system requirements and performance.

Regarding an analysis framework, the embodiments disclosed herein compute the free space based on a circular array in a plane within an obstacle ellipse center and measures the boundary distance error. For a low curvature cavity, a cross section of a uniformly distributed array may be approximated according to the following processes. For other types of cavities, integration of several view-points may be used.

A transmitter-receiver pair defines a region of acceptance. In the region of acceptance, certain echoes can be detected based on directivity and relative positioning, while other echoes are considered noise for a specific transmitter-receiver pair. Free space is generally identified or detected via the transmitter-receiver pair by determining the time of the first echo from an obstacle, which is reflected either on the acceptance region boundary or interior to it. The transmitter-receiver pair denigrates into two narrow beams for a very narrow acceptance angle, resulting in the same number of intersection points with the obstacle as the number of elements, i.e. number of transducers. For a very wide acceptance angle, the number of element-pair related ellipses is approximately proportional to the square of the number of elements or transducers.

Regarding a 2D mathematical framework, the embodiments disclosed herein rely on a 2D array of n elements being placed uniformly around a circle with a radius r. In one embodiment, the radius is 15 mm. One of ordinary skill in the art would understand that the radius may vary according to differing parameters and situations. Each element acceptance angle is $\phi$. Points outside of the circle are discarded. The array lies within an Ellipse $E_0$ with major axes a, b. The process computes the free spaced detected by the array as a union of geometrical objects based on the following values and parameters. Every element or transducer a in the array has a slice $s_{i,\phi}$ in the plane defined by the element's acceptance angle, which is essentially normal to the element's surface. Each element pair in the array produces a wedge from which the pair accepts reflections. The wedge is defined by the intersection of two slices, $s_{i,\phi}$ and $s_{j,\phi}$, and equation 9, shown in FIG. 19A for clarity.

In situations where i=j, the pair is the element itself and the wedge is a sector of slice $s_{j,\phi}$. To determine free spaced detected by pair $p_{i,j}$, the time of the first echo detected by the pair $p_{i,j}$ must be determined. The time and the pair combine to define an ellipse $E_P$, and the free space for this pair is the intersection of the wedge and ellipse $E_P$.

The following observation (Observation 1) is provided based on the processes disclosed herein. The first echo may be received from one of two possible cases: either it is at the point $x \in E_P$ where $E_P$ is tangent to $E_0$, or it lies at the extreme points of $\partial W_{i,j} \cap E_P$.

Observation 1 describes points needed to be located in order to find the free space discoverable by $p_{i,j}$. This is solved using the set of equations (equation 10 and equation 11) shown in FIGS. 19B and 19C for clarity, respectively.

Equation 10 requires that the intersection point belongs to the ellipse defined by the transmitter-receiver pair and the obstacle ellipse.

Equation 11 states that the obstacle ellipse and the transmitter-receiver pair are tangent.

In Equations 10 and 11, $p_1$, $p_2$ are the locations of the transmitter receiver pair and (u, v) is the mean, i.e. a center of the ellipse. Elements a, b are the major axes of the obstacle ellipse. Elements $a_\theta$, $b_\theta$, are the major and minor axis for the ellipse defined by a transmitter-receiver pair and a first echo point. Angle $\theta = \angle(p_1 - p_2)$, and the angle θ is the rotation angle of a transmitter receiver ellipse from the positive x-axis.

There are three equations for elements $x_0$, α, and $a_\theta$, which are solved numerically. Signs (i.e. positive and negative root solution of a basic ellipse equation) are selected to produce the smallest ellipse, which is intersected with acceptance region $W_{i,j}$, and the free space is computed using Observation 1. If the first echo is in the interior of the wedge, it results from $E_P$ being tangent to the obstacle ellipse, the normal is equal at the tangent point, and the curvature of the obstacle ellipse must be smaller than that of $E_P$. This relationship is true for any smooth reflecting surface. Based on the above relationships, the following Theorem is provided: let x is the point of the first echo of the pair $P_{i,j}$, and if $x \in W_{i,j}$ and $x \notin \partial W_{i,j}$, then $\Delta x = \Delta E_P(x)$ and $\Delta^2 x \le \Delta^2 E_P(x)$ (hereinafter "Theorem").

In one aspect, the disclosed subject matter is configured to identify free spaced based on at least one of a spherical pressure wave, a directivity, or a signal intensity. In general, free space is at the system noise level, while actual echoes are at least five times larger. This relationship and calculation is dictated by the system SNR. All of the transducers emit a spherical pressure wave. This wave is attenuated at certain directions by the directivity. Along the line which starts at the transducer center and is tangent to its normal (i.e. transducer axis), there is no attenuation at all. If this line is rotated, points in space along this rotated line will feel less pressure from the wave compared to those on the axis line. This change is the result of directivity. The signal intensity, as used in this aspect, is defined as the measured signal in the receiving transducer. The signal intensity is a direct result of the pressure wave that is reflected from one or more reflectors in space, where the reflectors are usually tissue in this application.

A complete form of the signal is $P_1(x_{sc})$, as shown in equation 12 of FIG. 19D.

The signal transmitted from s and received by re is calculated based on a sum of reluctances from all scatterers, as shown by equation 13 of FIG. 19E.

In the classic delay (i.e. the usual DAS beamformer) and sum(DAS) beam former $P_1(x_{sc})$ is estimated by summing ψ(s, re, t) over all (N(N+1))/2 transducer element pairs (s, re) signals at the point sc yielding equation 14 of FIG. 19F.

Equation 14 represents the sum of all contributions from the transmission and receiver pairs for a specific point in space at predetermined periods in time. The peak envelope of a signal s operator is denoted as ε(s). The envelope is calculated using an absolute value of the signal, and taking a maximum within a relatively reduced time window ΔW (wavelength wide). The transducer/receiver element pair (s, re) and the scatterer (sc) define an ellipsoid E(sc, s, re) passing through a point $x_{sc}$, with foci at $x_s$ and $x_{re}$. Due to the acoustic impedance of blood being lower than the myocardium, all points $sc \in V_{BP}$ within the blood-pool or at the blood pool/myocardial interface $P_1(x_{sc}) \ge 0$. It is assumed that all reflectors are specular (i.e. ignoring or neglecting speckles). Therefore, if there are no signals (i.e. below noise level) at a certain time T received at a predetermined pair (s, re), then all the points T are defined as shown below-by-in Equation 15 of FIG. 19G.

In Equation 15, T corresponds to all the points on the ellipsoid $E(\vec{x}, s, re)$ that are of zero reflectance or are in the free space. At $t = t_d$, $\varepsilon(\varphi) = P_0$ and ε(S) is bound by it from above. Based on these relationships, Equation 16 of FIG. 19H is provided.

For all points $sc \in V_{BP}$ and transmitter receiver pairs (s, re), the signal is defined by equation 17 of FIG. 19I.

Because ε(S) is positive by definition, and the portion of Equation 14 results from ignoring or neglecting speckling, then equation 18 of FIG. 19J is also is true.

The BRV is defined for all points $\vec{x}$ as shown in equation 19 of FIG. 19K.

Figure 11A:
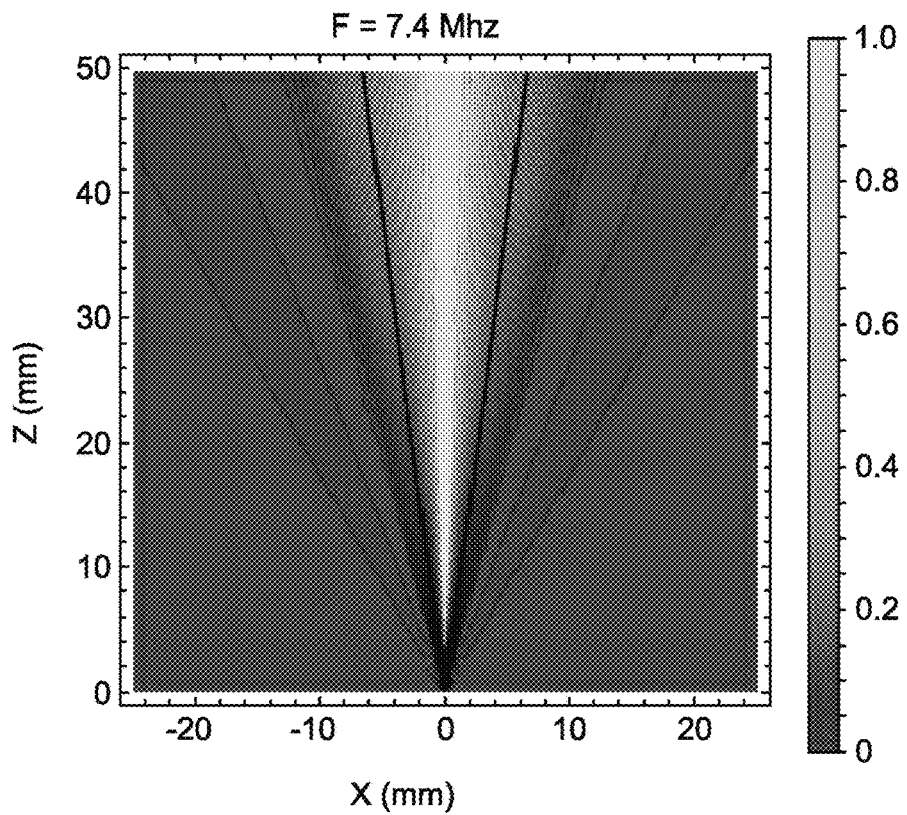
FIG. 11A illustrates a narrow beam pattern according to one embodiment.
Figure 11B:
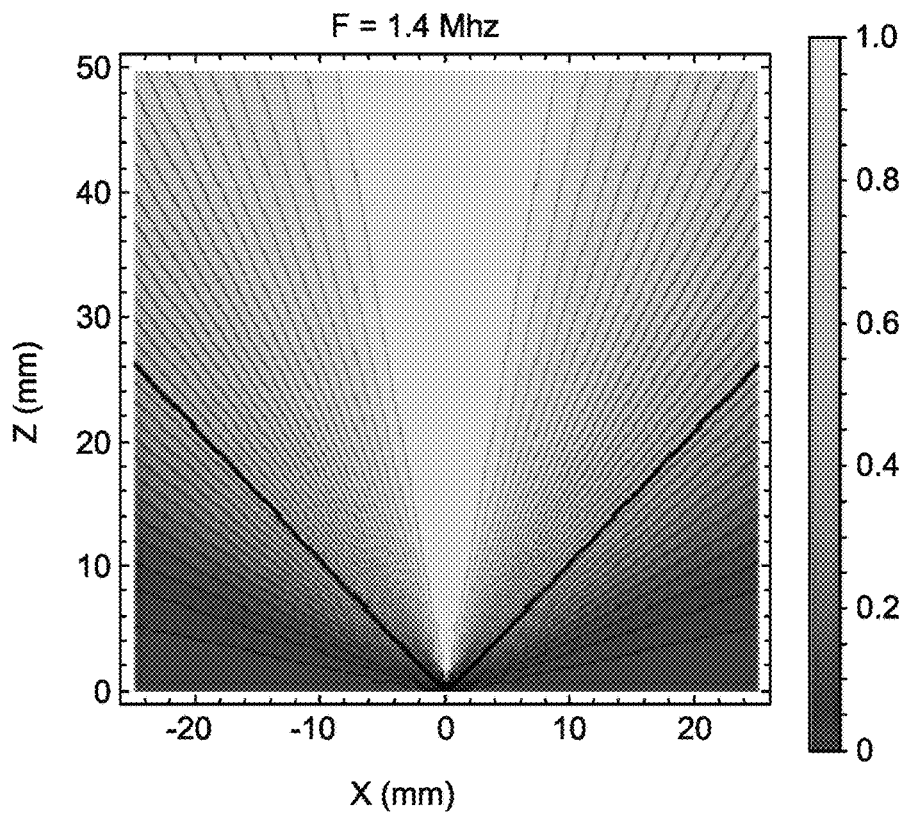
FIG. 11B illustrates a wide beam pattern according to one embodiment.
Figure 11C:
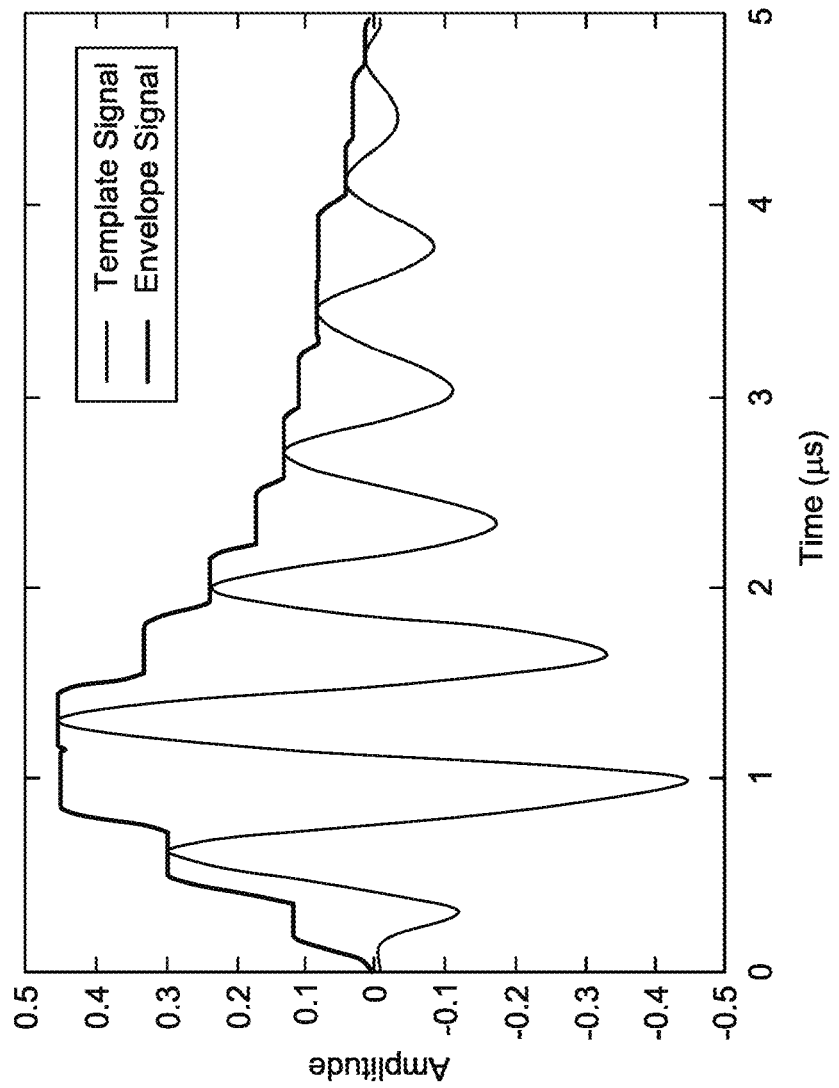
FIG. 11C illustrates an amplitude of a template signal and an envelope signal over time.

FIG. 11A illustrates a narrow beam pattern having a frequency of 7.4 Mhz, and FIG. 11B illustrates a wide beam pattern having a frequency of 1.4 Mhz. The values on the right-hand side of FIGS. 11A and 11B indicate normalized intensity. The narrow beams are generally used in a first echo detection mode. In other words, the space being navigated is free until the beams hit a first echo. This information is added to information regarding a wide beam scan. The narrow beams provide greater definition and analysis inside of the pulmonary veins. FIG. 11C illustrates an amplitude of a template signal and an envelope signal over time. In FIG. 11C, the signal bandwidth is 77%.

Figure 12A:
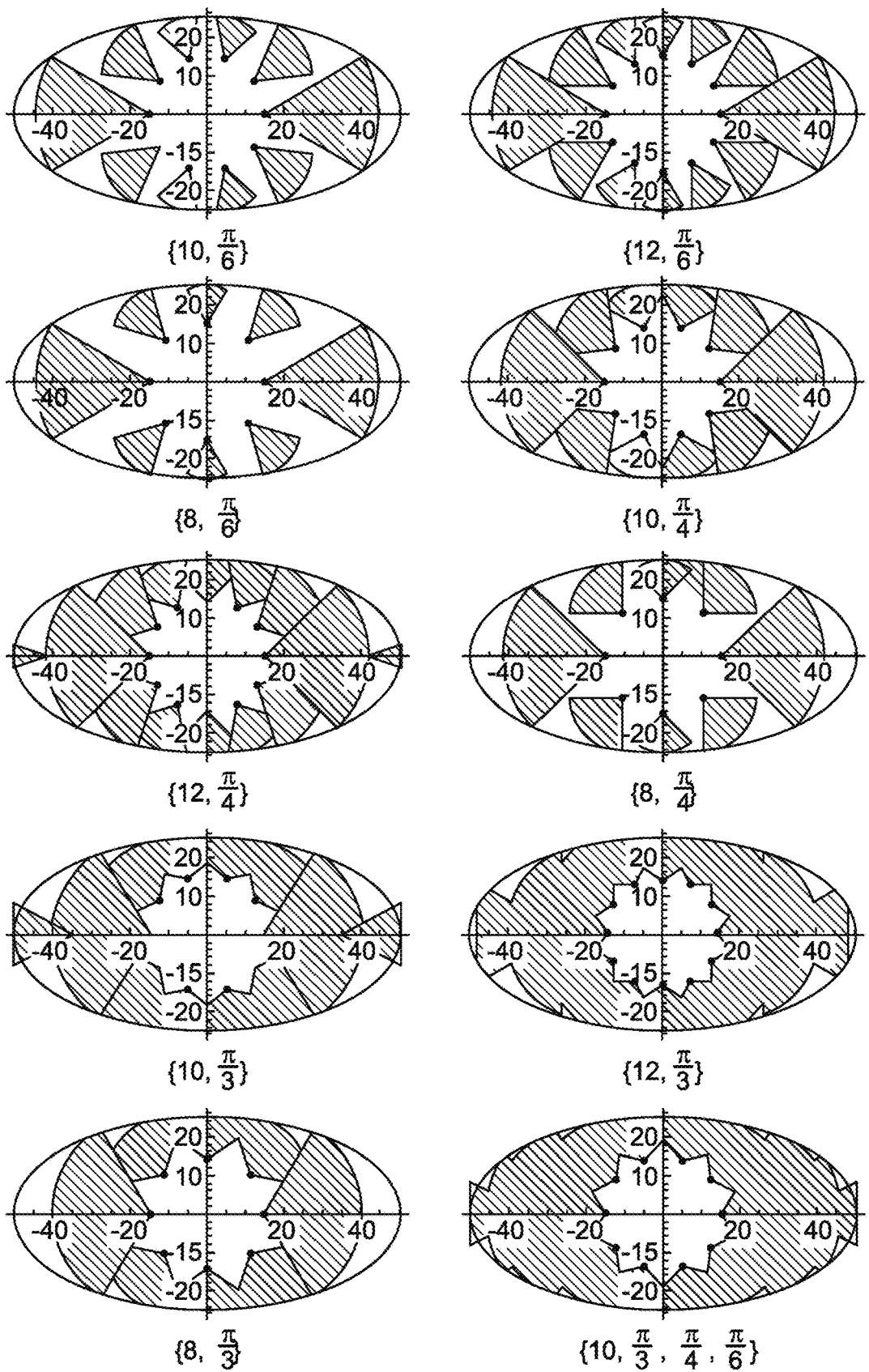
FIG. 12A illustrates multiple arrays, ellipse obstacles, and free spaces according to one imaging technique.
Figure 12B:
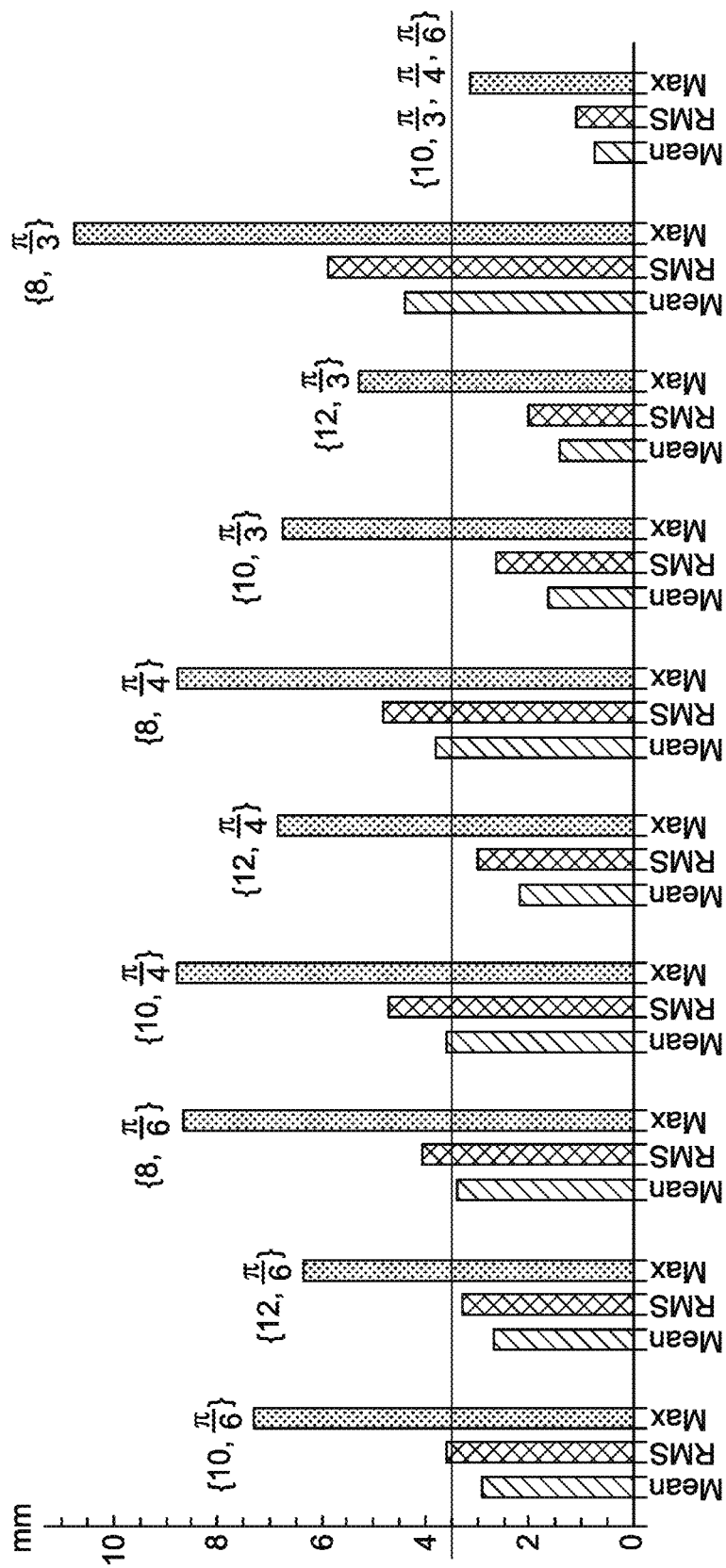
FIG. 12B illustrates the mean, RMS, and maximal values for the ellipse distance for various pairs of elements and acceptance angles.

FIG. 12A illustrates multiple arrays, ellipse obstacles (indicated as the outer oval ring), and free spaces (indicated by shading). The arrays are defined at the innermost points defined by the free spaces, and shown by dots. Each subset of images in FIG. 12A indicates the number of elements as the first value in the brackets and the acceptance angle as the second or subsequent values in the brackets. FIG. 12B illustrates the mean, RMS, and maximal values for the ellipse distance for each pair of elements and acceptance angles. Regarding FIGS. 12A and 12B, a simulation was carried out with an array having a radius of 15 mm for 8, 10, and 12 elements operating at acceptance angles of π/3, π/4, and π/6. The obstacle ellipse has a major axis x having a 50 mm range and a major axis y having a 25 mm range. This ratio of the major axes is larger than a typical left atrial, but illustrates the capabilities of the disclosed subject matter.

The distance, referred to as the ellipse distance, is measured from discovered free space to sampled points along the obstacle ellipse, which are each less than 0.25 mm apart. The 0.25 mm value is a sampling choice that bounds the error measurement. One of ordinary skill in the art would understand that this value can be smaller or larger. FIG. 12A illustrates the resulting free space regions detected by each array and acceptance angle pair in shaded regions, and also shows the union of all three acceptance angles for a 10-element array. This configuration illustrates an example of a multi-frequency operation. In FIG. 12B, the horizontal line corresponds to approximately 3.5 mm, and indicates the accuracy of these configurations.

Figure 13A:
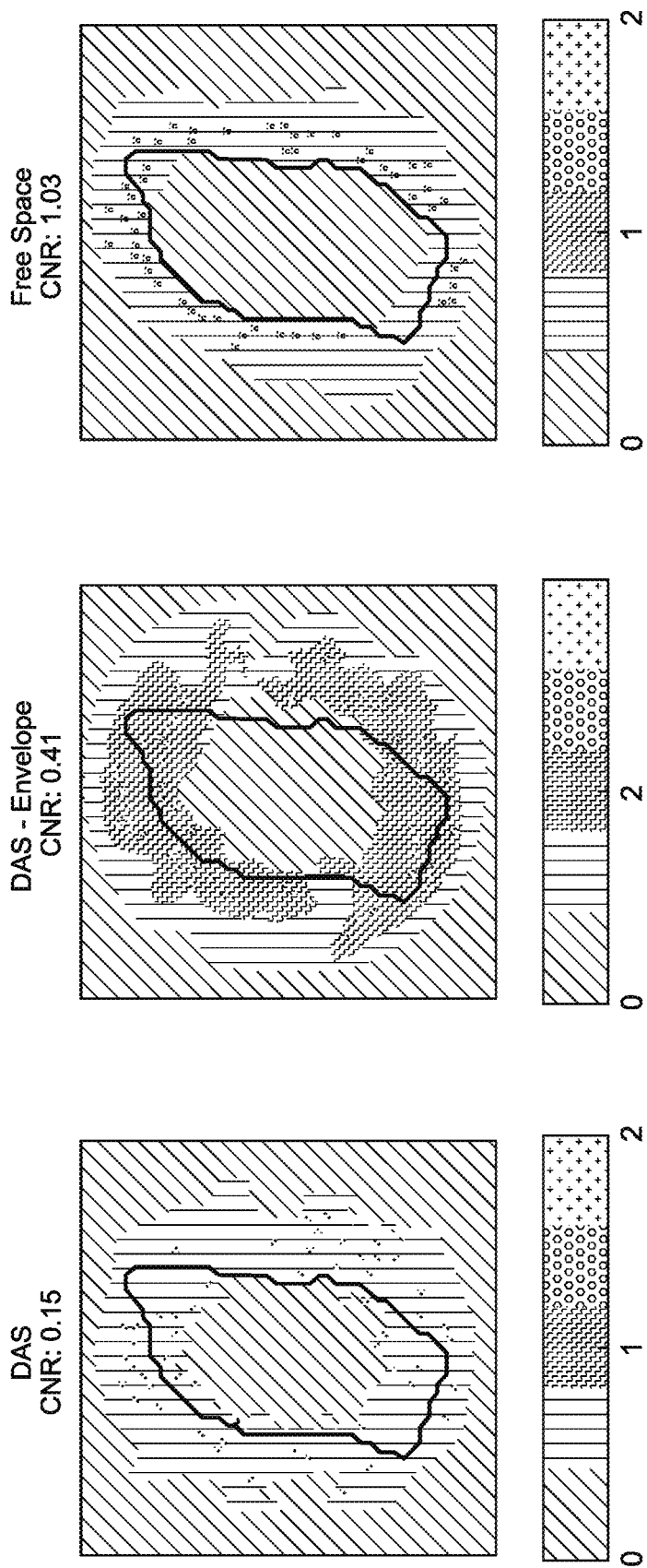
FIG. 13A illustrates pixel intensities around a boundary in a given slice for three various imaging methods.
Figure 13B:
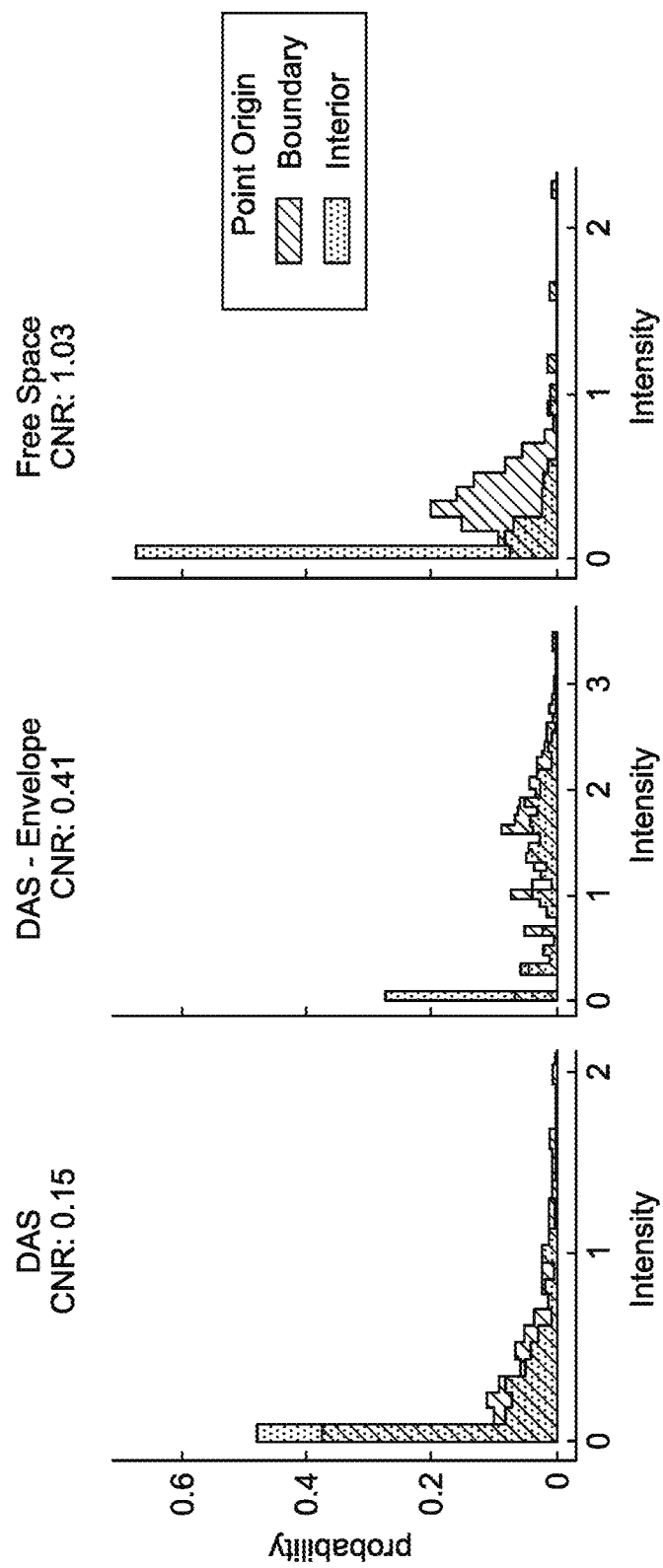
FIG. 13B illustrates the respective distributions for the imaging methods of FIG. 13A.

In a simulation experiment, the free space method was compared to the DAS method in silicon. To provide coherent summation, the locations of elements are assumed to be precisely known. A spherical array of a 15 mm radius with 64 elements inside a left atrium was segmented from a computerized tomography (CT). The volume is a 10 cm side cube, divided into $50^3$ voxels using a 2 mm 3D grid. Reflectors are sampled in the grid inside a 6 mm thick shell around the atrial boundary. A template hydrophone record signal (i.e. 1.4 MHz, 77% bandwidth) is used for the simulation and also includes a time scaled version for a higher frequency (7.4 MHz). This corresponds to the value from FIG. 11C. No additive noise is used to assess the optimal algorithm performance. According to Equation 12 below, the template signal is delayed and summed for each transmitter receiver pair and reflector. Those generated RF signals are used to compute the BRV for wide beams and the first echo for the narrow beams. Imaging volumes are also computed using DAS and envelope DAS. The envelope is computed as a max absolute value within a window corresponding to the cycle length. Pixel intensities of 4 mm are gathered around the boundary in a given slice for the three methods as shown in FIG. 13A (which is for a free space method), and the respective distributions were compared as shown in FIG. 13B. As shown in FIG. 13A, closed loops form boundaries for each slice. The free space boundary suffers less from array processing artifacts and has a much higher contrast to noise ratio (CNR) compared to the DAS and DAS-envelope methods. The value on the bottom of FIG. 13A is an intensity value.

Figure 14B:
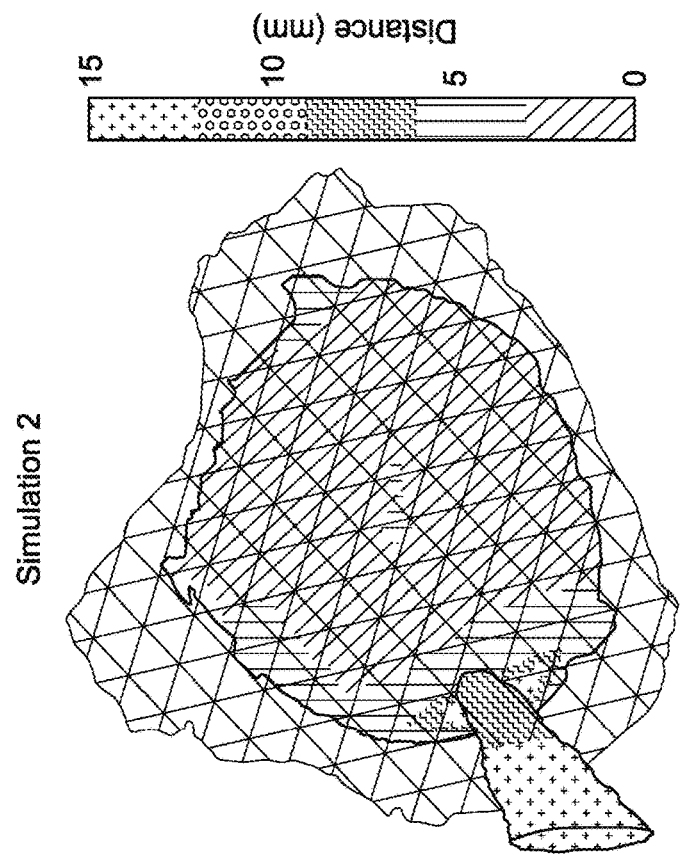
FIG. 14B illustrates reconstruction results according to a second simulation.
Figure 14A:
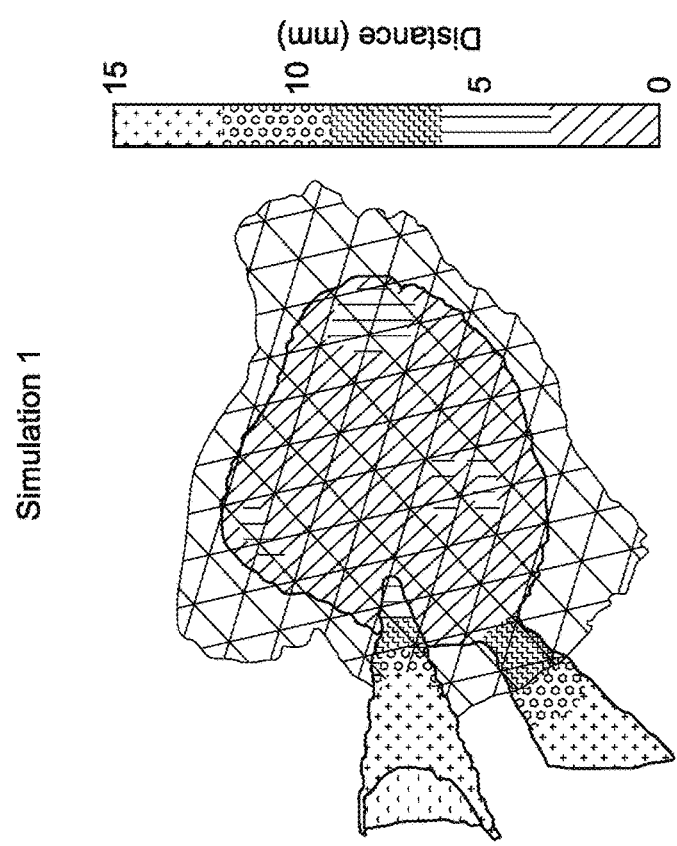
FIG. 14A illustrates reconstruction results according to a first simulation.

FIGS. 14A and 14B illustrate reconstruction results of two simulations using a free space method. The reconstruction is close to the left atrium body while the pulmonary vein locations are detectable given the bulbs resulting from the narrow beams. Mesh reconstruction is modeled according to distance to reflectors. An outer mesh is illustrated and shows various patches of varying distance to the reconstruction. All of the distances were clipped at 15 mm. The median and median absolute deviation (MAD) of distances (in mm) are provided. In Simulation 1, the median distance was 2.27 mm and the MAD was 1.3 mm from the detected boundary to the reflectors. In Simulation 2, the median distance was 2.78 mm and the MAD was 1.8 mm from the detected boundary to the reflectors. From the reflectors to the boundary, Simulation 1 resulted in a median distance of 3.78 mm and a MAD of 1.68 mm, and Simulation 2 resulted in a median distance of 3.54 mm and 1.53 mm. The distances from the reflectors to the boundary were computed from the middle of the atria wall shell, which is 2 mm away from the endocardium.

Figure 15A:
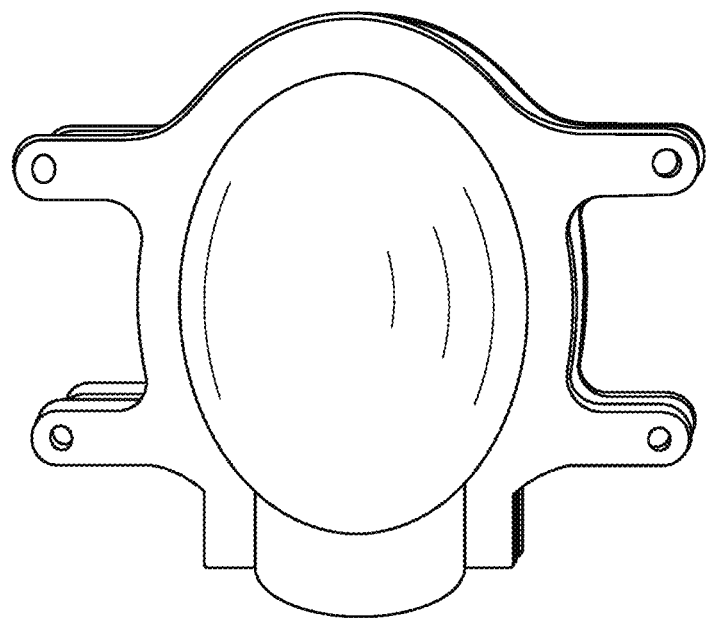
FIG. 15A illustrates an ellipsoid phantom according to one embodiment.
Figure 15B:
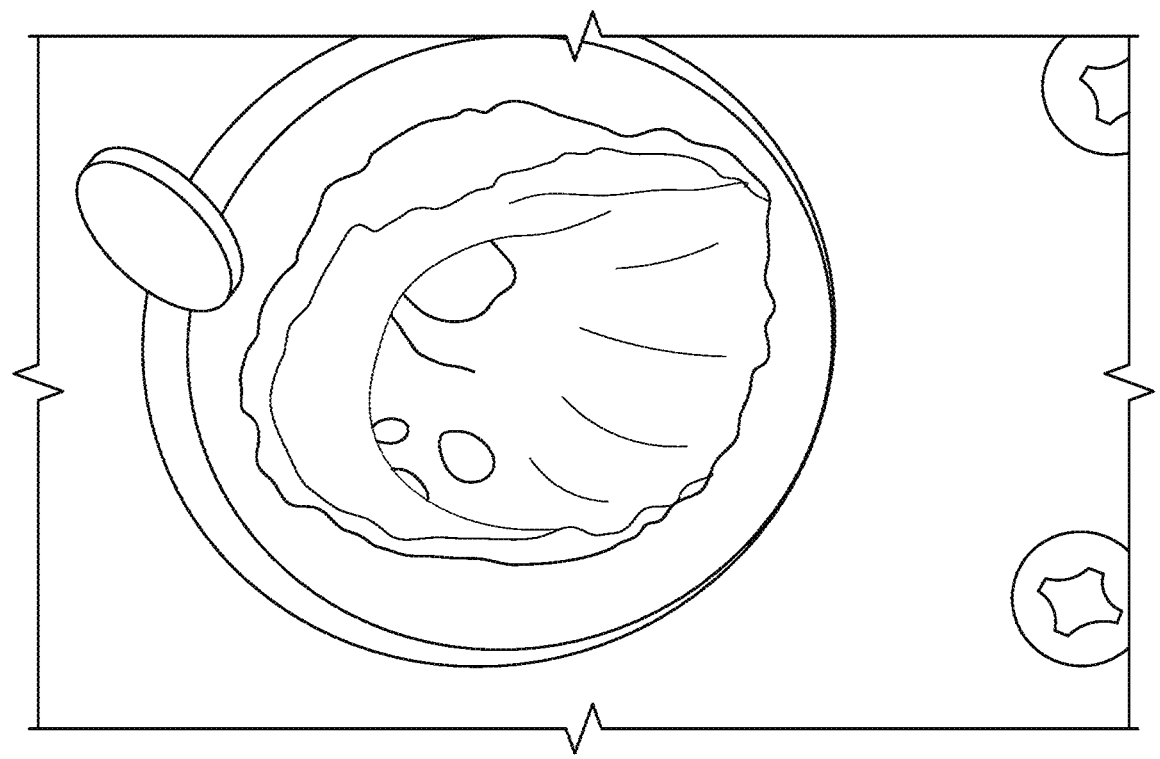
FIG. 15B illustrates left atrium silicon phantom according to one embodiment.

In another aspect, additional in-vitro experiments were conducted with a disperse 64-element piezoelectric (PZT-5H) transducer array. In these experiments, each element has a size of 1×1×0.3 mm and is mounted on splines of a spherical basket, as illustrated in FIG. 2. Each transducer element has two resonance frequencies: a first at about 1.4 MHz and a second at about 7.4 MHz. The location of the elements in the array are measured by an optical system having approximately 1.0 mm accuracy. The array is operated using a National Instruments (NI) acquisition system configured to generate arbitrary pulse-shape excitations and receiving echoes from all elements in the array simultaneously. The catheter is placed in a water bath designed to simulate a blood pool, and enclosed in an ellipsoidal plastic enclosure designed to simulate the walls of a cardiac chamber. FIG. 15A illustrates an ellipsoid phantom and FIG. 15B illustrates a left atrium silicon phantom. Cardiac-like wall motion is generated by continuously pumping water in and out of the chamber. Direct transmit-receive signals, which did not experience reflection from the moving walls are eliminated by subtracted long-time signal averages. The signals are averaged over multiple acquisitions. In one aspect, the acquisitions occur about fifteen times for low frequency and three times for high frequency. This produces a SNR value of at least four.

Figure 16A:
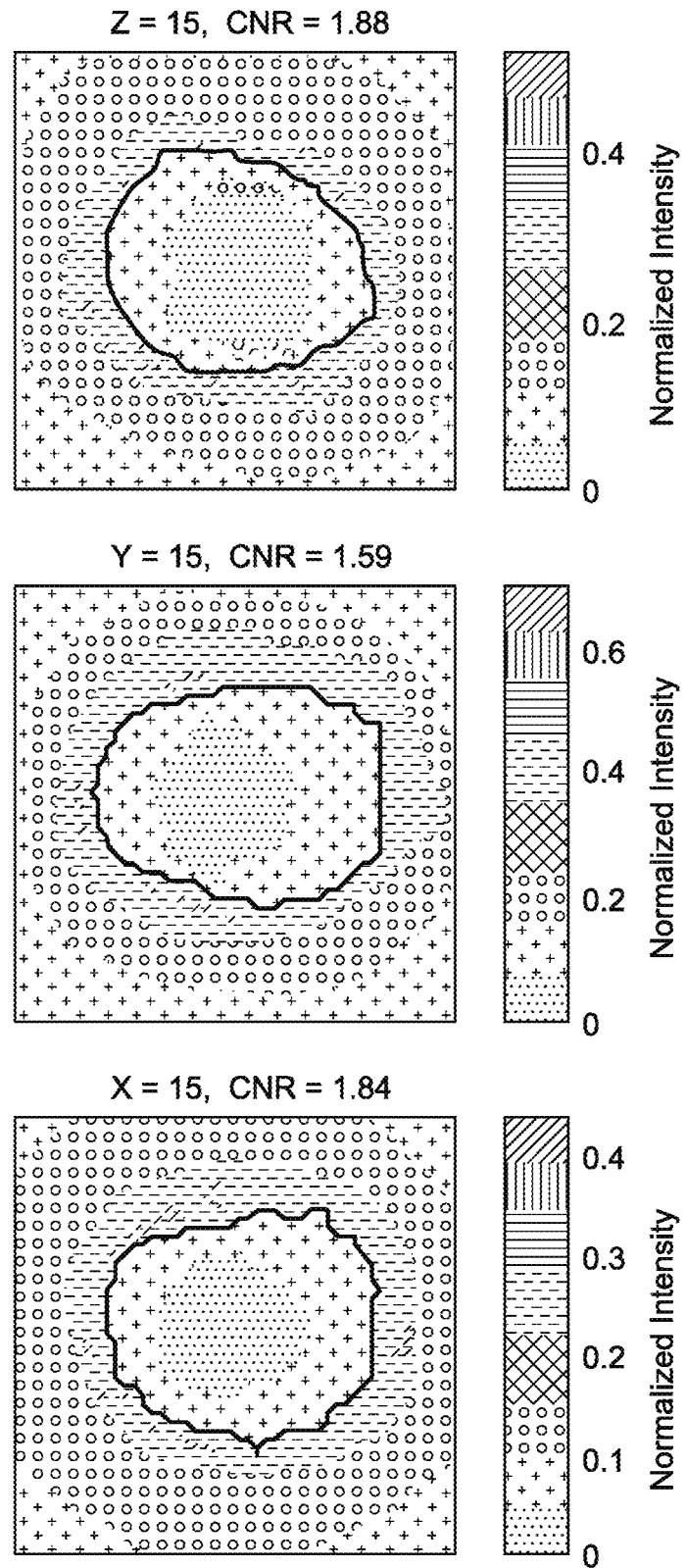
FIG. 16A-16C each illustrate various slices through a detected boundary as computed by a free space algorithm at different areas along different axes.
Figure 16B:
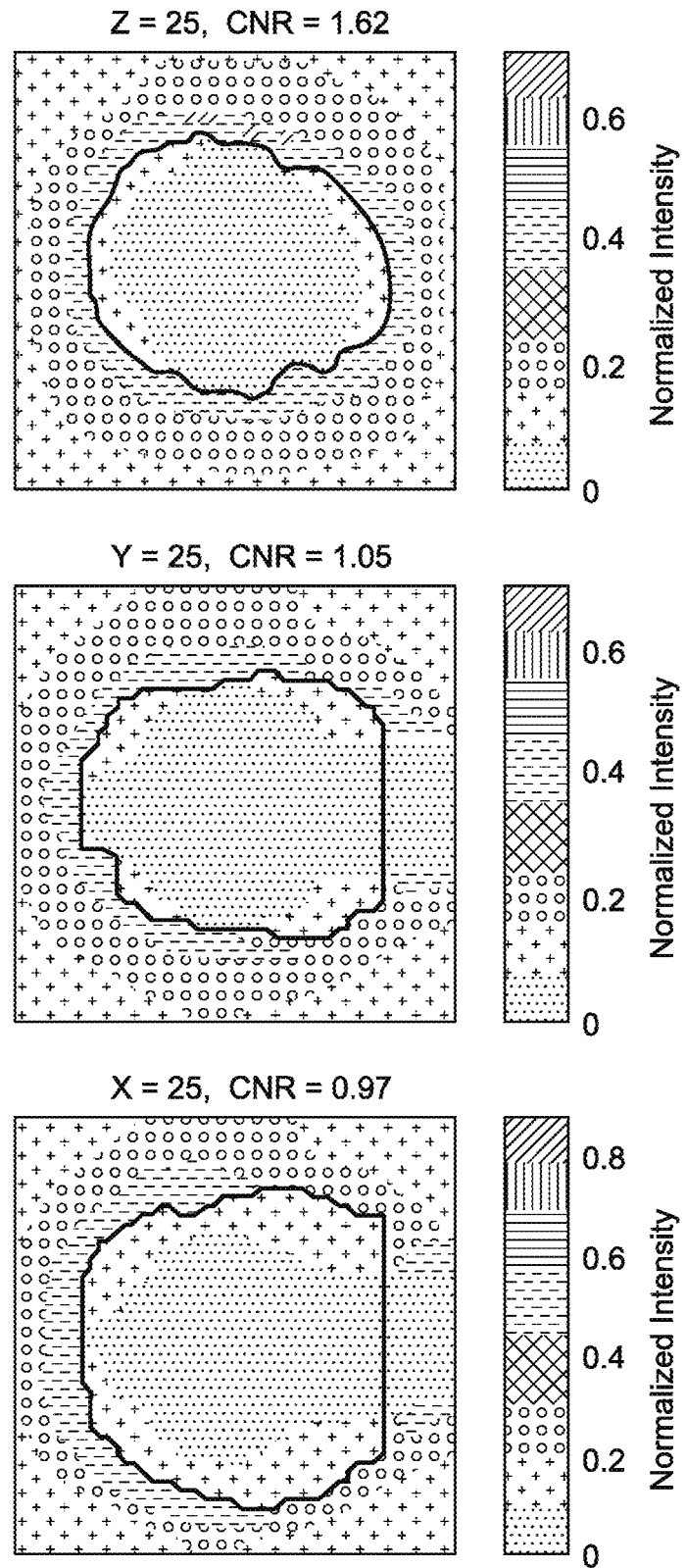
Figure 16C:
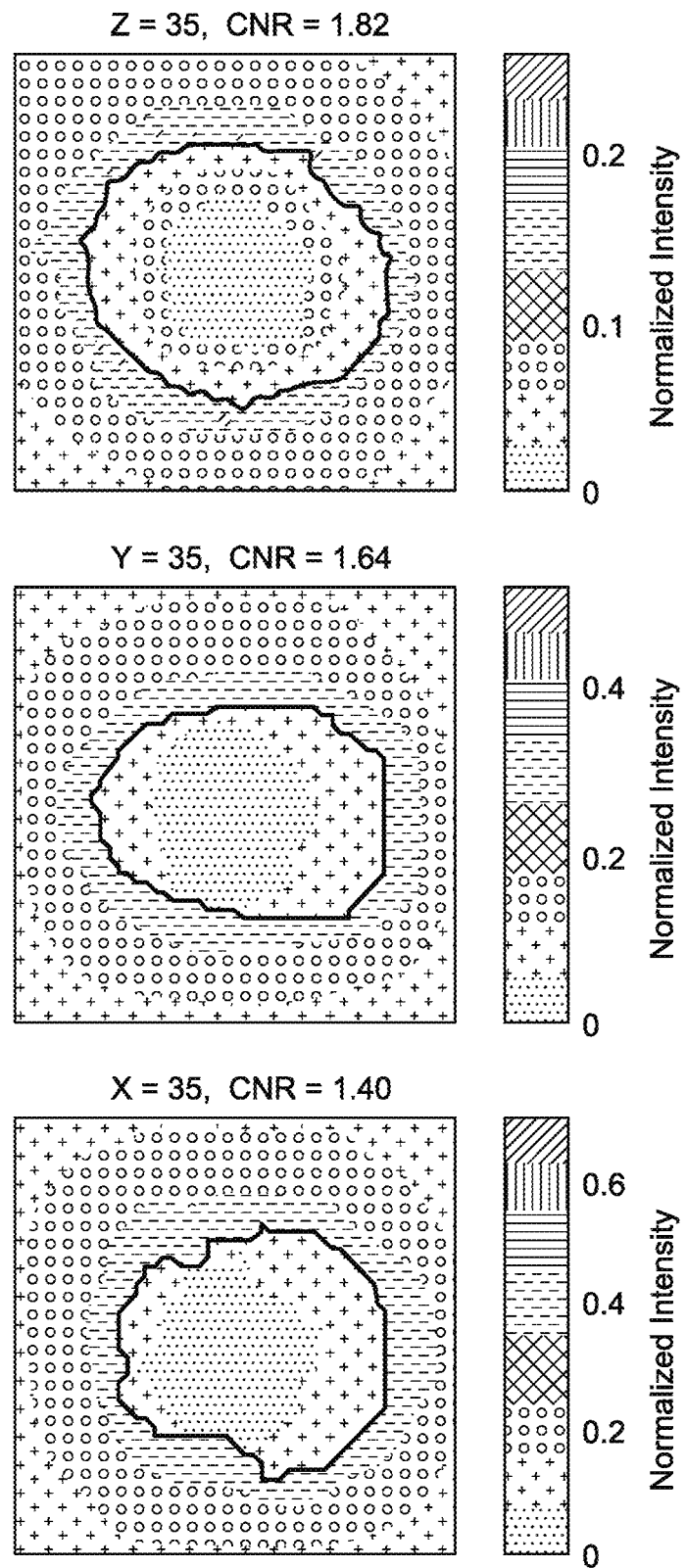

In another aspect, additional ellipsoidal phantom experiments were carried out using the disclosed subject matter. In this experiment, the catheter is placed inside a silicon ellipsoidal shaped phantom that is filled with water. The phantom has radii of 35 mm, 32.5 mm, and 22.5 mm. In one aspect, acquisition was performed using 1.4 MHz wide beams (i.e. 2.5 cycles). The term cycles as used here refers to a transmit signal made of a number of sinusoidal cycles. Signal dynamic range was adjusted using square root signal compression. An ellipsoid was then fit to the algorithm detected boundary. FIGS. 16A-16C include multiple slices through a detected boundary computed by the free space algorithm at different points along different axes. These FIGS. 16A-16C illustrate the result of a BRV operator. In each of FIGS. 16A-16C, the detected boundary is illustrated as the closed loop surrounding the generally central shaded mass. Each of FIGS. 16A-16C illustrate a series of slices through the recorded volume, perpendicular to the x, y, z axes at 15 mm, 25 mm, and 35 mm. CNR is computed for a sub-volume of 6 mm around the boundary. Because the phantom is not a complete ellipsoid, the error distribution is skewed. The median and MAD were computed. The MAD estimates standard deviation in a Gaussian distribution with a factor of approximately 1.5. The measured radii were 36 mm for FIG. 16A, 33.4 mm for FIG. 16B, and 25.5 mm for FIG. 16C. The ellipsoid median deviation was 1.4 mm and the MAD was 0.6283 mm.

In another aspect, additional left atrium shaped silicon phantom experiments were carried out, as illustrated in FIG. 15B. In these experiments, scans were obtained using narrow beams and wide beams, and the free space algorithm detected boundary points of the phantom. Those points were used as an input for a model-based fast anatomical mapping smoothing algorithm (mFam).

The reconstructed anatomy was manually aligned with a ground truth CAD mesh. The distance of each vertex of the smoothed surface to the corresponding ground truth mesh was computed. The resulting mean was 4.2±4.4 mm (as compared to 3.5 of FAM), the median was 2.6 mm, the MAD was 1.77 mm, and the RMS was 6.1 mm.

Figure 17A:
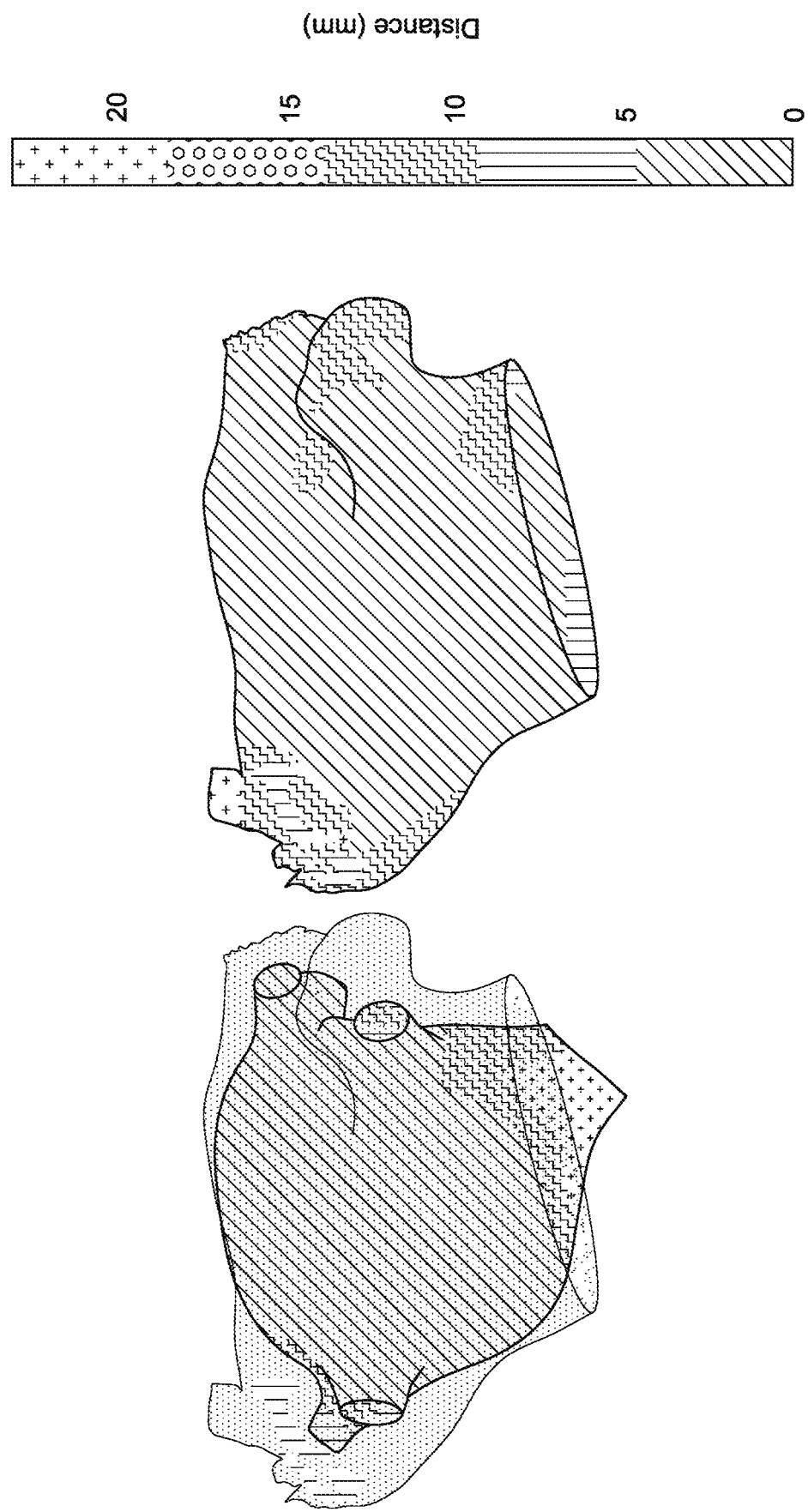
FIG. 17A illustrates reconstruction results and errors according to different techniques.
Figure 17B:
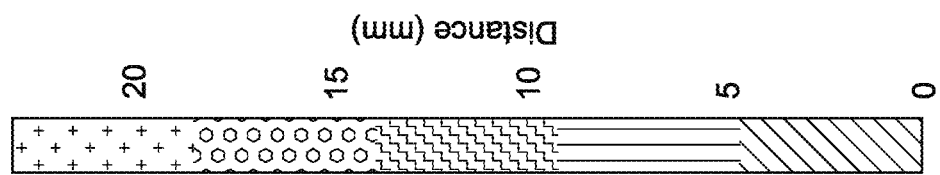
FIG. 17B illustrates reconstruction results and errors according to different techniques.
Figure 17B:
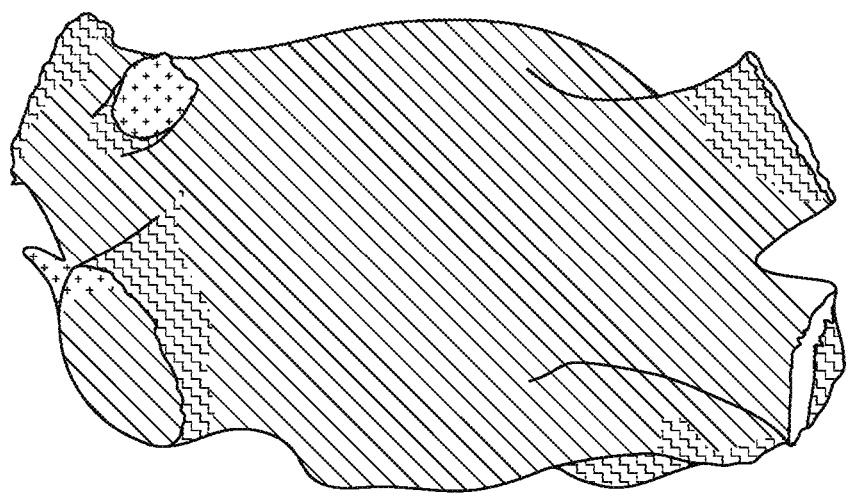
Figure 17B:
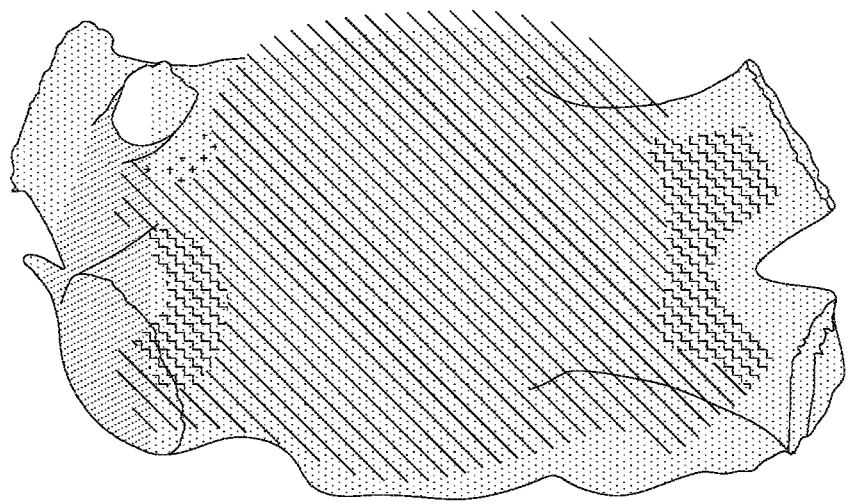

The reconstruction result and error are illustrated in FIGS. 17A and 17B. FIGS. 17A and 17B illustrate model-based smoothing using BRV, a segmentation over the BRV, and using the segmented boundary as an input to the mFam algorithm. The left-hand image in FIGS. 17A and 17B is the detected boundary-based model to CAD distances in mm.

The right-hand image in FIGS. 17A and 17B is the CAD ground truth image with distances to the reconstruction. The resulting model is close to the phantom, while the detected pulmonary veins are consistent with the CAD mesh, but the size estimation is insufficient, which results in large errors in those areas. This issue can be addressed by conducting additional acquisitions. Some errors experienced in the left atrium reconstruction were caused by inter-sensor distances not being fixed in position, which can cause errors up to several millimeters in sensor positions, which are then translated into reconstruction errors. The disclosed subject matter improves calibration of these distances to sub-millimeter accuracy.

In summary, the elements in sparse arrays are not sub-wavelength distance apart, and therefore fail the Nyquist criterion. Determining element positions to sub-wavelength accuracy is difficult, which causes additional errors particularly in coherent summation. Distinctions between the disclosed processes, systems, apparatuses, and methods and DAS were described above with respect to the experiments, such as the in-silico experiments, as well as by the array processing related artifacts that are apparent in the PSF and for distinguishing nearby reflectors. This is illustrated in FIGS. 10A-10F.

The subject matter disclosed herein and the envelope signal improves detection results significantly, as shown by at least FIGS. 13A and 13B. In one aspect, in order to match clinical system performance, at least ten elements operating at a wide angle of $\pi/3$ are required, as is present at any given 2D slice. Unlike other systems that only use narrow beams and sample the endocardial surface linearly, the system disclosed herein samples at a quadratic rate, as it examines echoes received by transducer pairs, while gaining additional normal and curvature information by the Theorem disclosed herein. Compared to existing systems, which require one minute per region for an accuracy of 3 mm, the disclosed subject matter accurately maps the entire endocardium within fewer acquisitions performed in real time. In one embodiment, the scans described herein take less than 16 ms.

The disclosed subject matter is not limited to the left atrium or any heart chamber. The disclosed subject matter can be used in a variety of application, including applications that utilize an array of elements to analyze features of an object, such as a chamber.

In summary, in one aspect, a catheter is provided that allows for detecting electrical activity with real-time imaging and tracking of cardiac electrical wave propagation, which enables mapping of complex arrhythmia and reduced the time required to provide reliable images and data.

Generally, a specific time in a signal corresponds to a time of flight of the catheter in the cavity, which in turns defines an entire ellipsoid in space. Due to the unique structure of the heart, a narrow cavity such as a pulmonary vein will not be included in the ellipsoid and thus be hard to detect by known mapping methods. Using a narrow beam emission will overcome this issue due to its size, which easily fits inside narrow portions of the heart structure. Additional beams that have different directivity patterns rely on the same ellipsoid concept, and slices in the acceptance angle are defined by the beam directivity. Therefore, the combination of beams provides additional information about the boundary shape with a relatively small downside of acquisition time. For example, an additional acquisition time of 70 microseconds per element may be required.

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. A device comprising:
   a catheter configured to be inserted into an intra-body cavity of a patient;
   an ultrasonic transducer array comprising a plurality of multi-frequency ultrasonic transducers arranged on the catheter,
   each transducer of the plurality of multi-frequency ultrasonic transducers configured to transmit a wide beam ultrasonic signal and a narrow beam ultrasonic signal, wherein the wide beam ultrasonic signal has a lower frequency than the narrow beam ultrasonic signal, and
   each transducer of the plurality of multi-frequency ultrasonic transducers configured to receive wide beam echo signals and narrow beam echo signals in response to the wide beam ultrasonic signal and the narrow beam ultrasonic signal; and
   a processor configured to:
   time-align at least one of the received wide beam echo signals and at least one of the received narrow beam echo signals, and
   detect free space of the intra-body cavity by determining whether a minimum of a combination of the time-aligned signals is below a threshold.

2. The device of claim 1, wherein the processor is configured to detect the free space by determining a bounding reflection value (BRV), and the BRV indicates whether a specific point in space within the intra-body cavity is in the free space.

3. The device of claim 1, wherein the ultrasonic transducer array comprises at least 64 multi-frequency ultrasonic transducers.

4. The device of claim 1, wherein the narrow beam ultrasonic signal has a frequency in a range of 12 MHz to 16 MHz.

5. The device of claim 1, wherein the wide beam ultrasonic signal has a frequency in a range of 1 MHz to 3 MHz.

6. The device of claim 1, wherein the wide beam ultrasonic signal has a beam width of at least 40 degrees.

7. The device of claim 1, wherein the narrow beam ultrasonic signal has a beam width in a range of 4 degrees to 12 degrees.

8. The device of claim 1, wherein the intra-body cavity includes a vein.

9. The device of claim 1, further comprising a monitor configured to display the free space.

10. The device of claim 1, wherein the intra-body cavity is a cardiac chamber.

11. The device of claim 1, wherein the processor is configured to identify the free space based on at least one of signal directivity or signal intensity.

12. A method comprising:
inserting a catheter into an intra-body cavity of a patient, the catheter comprising an ultrasonic transducer array including a plurality of multi-frequency ultrasonic transducers;
transmitting a wide beam ultrasonic signal and a narrow beam ultrasonic signal from each of the plurality of multi-frequency ultrasonic transducers, wherein the wide beam ultrasonic signal has a lower frequency than the narrow beam ultrasonic signal;
receiving wide beam echo signals in response to the wide beam ultrasonic signal and narrow beam echo signals in response to the narrow beam ultrasonic signal;
time-aligning at least one of the received wide beam echo signals and at least one of the received narrow beam echo signals; and
identifying free space of the intra-body cavity by determining whether a minimum of a combination of the time-aligned signals is below a threshold.

13. The method of claim 12, wherein the ultrasonic transducer array comprises at least 64 multi-frequency ultrasonic transducers.

14. The method of claim 12, wherein the narrow beam ultrasonic signal has a frequency in a range of 12 MHz to 16 MHz.

15. The method of claim 12, wherein the wide beam ultrasonic signal has a frequency in a range of 1 MHz to 3 MHz.

16. The method of claim 12, wherein the wide beam ultrasonic signal has a beam width of at least 40 degrees.

17. The method of claim 12, wherein the narrow beam ultrasonic signal has a beam width in a range of 4 degrees to 12 degrees.

18. The method of claim 12, wherein the intra-body cavity comprises a vein.

19. The method of claim 12, further comprising providing information regarding the free space to a display.

20. The method of claim 12, further comprising detecting the free space by determining a bounding reflection value (BRV), wherein the BRV indicates whether a specific point in space within the intra-body cavity is in the free space.

* * * * *

UNITED STATES PATENT AND TRADEMARK OFFICE
CERTIFICATE OF CORRECTION

PATENT NO. : 11,937,975 B2
APPLICATION NO. : 17/025622
DATED : March 26, 2024
INVENTOR(S) : Alon Baram et al.

It is certified that error appears in the above-identified patent and that said Letters Patent is hereby corrected as shown below:

On the Title Page

In Item (74), under "Attorney, Agent, or Firm", in Column 2, Line 1, delete "Volpe Koenig P.C." and insert -- Volpe Koenig --, therefor.

In the Specification

In Column 2, Line 43, delete "FIG." and insert -- FIGS. --, therefor.
In Column 7, Line 19, delete "p0" and insert -- $p_0$ --, therefor.
In Column 7, Line 31, delete "x$_{re.}$" and insert -- $x_{re}$ --, therefor.
In Column 7, Line 44, delete "P1" and insert -- $P_1$ --, therefor.
In Column 8, Line 50, delete "P1($x_{sc}$)=0" and insert -- $P_1(x_{sc})=0$ --, therefor.

In Column 10, Line 30, delete " $Dir(\Theta, ka) \propto \frac{2J_1(ka\sin\Theta)}{ka\sin\Theta}$ " and insert
-- $Dir(\theta, ka) \propto \frac{2J_1(ka\sin\theta)}{ka\sin\theta}$ --, therefor.

In Column 13, Line 20, delete "P1($x_{sc}$)" and insert -- $P_1(x_{sc})$ --, therefor.
In Column 13, Line 31, delete "fora" and insert -- for a --, therefor.
In Column 13, Line 40, delete "P1($x_{sc}$)" and insert -- $P_1(x_{sc})$ --, therefor.

In Column 13, Line 60, delete " $Dir(\Theta, ka) = \frac{2, J_1(ka\sin\theta)}{ka\sin\theta}$ " and insert
-- $Dir(\theta, ka) = \frac{2J_1(ka\sin\theta)}{ka\sin\theta}$ --, therefor.

In Column 14, Line 67, delete "a" and insert -- $e_i$ --, therefor.
In Column 15, Line 3, delete "pair" and insert -- pair $p_{i,j}$ --, therefor.

Signed and Sealed this
Twenty-second Day of October, 2024

Katherine Kelly Vidal
*Director of the United States Patent and Trademark Office*

CERTIFICATE OF CORRECTION (continued)
U.S. Pat. No. 11,937,975 B2

In Column 15, Line 5, delete "$s_{i,\phi}$and $s_{i,\phi}$, and" and insert -- $s_{i,\phi}$ and --, therefor.

In Column 15, Line 8, delete "$s_{j,\phi}$." and insert -- $s_{i,\phi}$. --, therefor.
In Column 15, Line 12, delete "wedge" and insert -- wedge $W_{i,j}$ --, therefor.
In Column 16, Line 7, delete "$P_1(x_{sc}$" and insert -- $P_1(x_{sc})$ --, therefor.
In Column 16, Line 25, delete "shown below-by-in" and insert -- shown in --, therefor.
In Column 16, Line 36, delete "is also is" and insert -- is also --, therefor.
In Column 16, Line 41, delete "Mhz," and insert -- MHz, --, therefor.
In Column 16, Line 42, delete "Mhz." and insert -- MHz. --, therefor.